United States Patent [19]

Yonezawa et al.

[11] Patent Number: 5,142,138

[45] Date of Patent: Aug. 25, 1992

[54] IMAGE READER INCLUDING PLURAL LIGHT STOPPING PLATES WITH APERTURES

[75] Inventors: Koichi Yonezawa; Michio Ito, both of Ohtsu, Japan

[73] Assignee: Toray Industries Inc., Tokyo, Japan

[21] Appl. No.: 627,591

[22] Filed: Dec. 14, 1990

[30] Foreign Application Priority Data

Dec. 18, 1989 [JP] Japan .................. 1-329007
Dec. 18, 1989 [JP] Japan .................. 1-329008

[51] Int. Cl.⁵ .......................... H01J 40/14; H01J 3/14
[52] U.S. Cl. ............................ 250/208.1; 250/237 R; 356/443
[58] Field of Search .............. 250/208.1, 552, 578.1, 250/237 R; 356/443, 444, 445, 446, 447, 448

[56] References Cited

U.S. PATENT DOCUMENTS 4,531,062  7/1985  Engemann et al. ............. 250/237 R
4,539,482  9/1985  Nose ................................ 250/208.1

Primary Examiner—David C. Nelms
Assistant Examiner—John R. Lee
Attorney, Agent, or Firm—Oblon, Spivak, McClelland, Maier & Neustadt

[57] ABSTRACT

An image reader of the present invention is provided with a plurality of photosensitive elements arranged one-dimensionally or two-dimensionally substantially in parallel with an image bearing member, and first and second stopping plates each of which has apertures at positions corresponding to the photosensitive elements, respectively, between the image bearing member and the photosensitive elements. The apertures of the second stopping plate are smaller in size than photosensitive surfaces of the photosensitive elements. The dimension of the apertures, the dimension of the photosensitive surfaces of the photosensitive elements and the distances between the first stopping plate, the second stopping plate and the photosensitive elements are set in a predetermined relation. This prevents the influence of the deviation of a mounting position of the photosensitive elements on a measuring error.

18 Claims, 16 Drawing Sheets

IMAGE READER INCLUDING PLURAL LIGHT STOPPING PLATES WITH APERTURES

BACKGROUND OF THE INVENTION

1. Field of the Invention

The present invention relates to an image reader for measuring light reflectivity or transparency of an image bearing member and more particularly to an improvement in performance and measuring accuracy of the image reader.

2. Description of the Prior Art

There are two types of image readers used conventionally in the field of printing: image readers which are intended for reading an image as detailed as possible to convert the image into processable data for a computer and the like, and image readers which are intended for measuring the area of either the white or black part of a binary monochrome image. The former is generally known as an image scanner. The latter is known as an ink pattern area meter, which is used for measuring the proportion (an ink pattern area rate) of a picture part (the part supplied with ink) in each portion of a printing plate or an original film to the whole printing plate or original film in order to establish the amount of ink supplied to a printing machine before a printing process.

The ink pattern area meter is intended for measuring an average ink pattern area of each of tens of small regions into which a printing picture plane is divided. Because of this intention, spatial resolution of the ink pattern area meter is low in comparison with the image scanner. The value of the spatial resolution is about several mm to 100 mm according to the printing machine to be employed. However, the accuracy of a measured value, that is, the absolute value of the difference between a real ink pattern area rate and the corresponding measured ink pattern area rate is severely required to be 1 to 5% in general. Particularly in printing of printed matter with a small ink pattern area rate (e.g., business forms), it is desirable to minimize errors in measurement.

An example of the image readers which are intended for measuring the ink pattern area rate is an apparatus disclosed in Japanese Patent Application Laid-Open No. 57-64102. A measuring head of this apparatus is described hereinafter referring to FIGS. 15 and 16. FIG. 15 is a cross-sectional view of the measuring head of the apparatus taken along the plane perpendicular to a main scanning direction X. FIG. 16 is a cross-sectional view taken along the line A—A of FIG. 15. In the description, a reference numeral or character which designates each component in the figures is provided with no subscript when the component is indicated as a representative of the whole (for example, photodiodes 6). A subscript is attached to the reference numeral or character when the individual components are specified. (For example, a plurality of members $6_{-1}$, $6_{-2}$, $6_{-3}$ ... $6_{-n}$ are referred to simply as $6_{-1}$ to $6_{-n}$.) The same is true for other figures.

As shown in FIGS. 15 and 16, the measuring head comprising a light source unit 2 and a light detecting unit 3 is provided above a printing plate 1 to be measured. The light source unit 2 comprises a pair of fluorescent lamps 4 each extending in the main scanning direction X and a reflecting plate 5 which covers the fluorescent lamps 4 from above down to the both sides thereof. The light detecting unit 3 comprises a plurality of photodiodes $6_{-1}$ to $6_{-n}$ arranged linearly in the main scanning direction X on a plane parallel to the printing plate 1, obstructors 7 disposed between the adjacent photodiodes $6_{-1}$ to $6_{-n}$ for partition, and a stopping plate 8 attached to the lower ends of the obstructors 7 in parallel with the printing plate 1. The stopping plate 8 is formed with apertures $9_{-1}$ to $9_{-n}$ at positions corresponding to the respective photodiodes $6_{-1}$ to $6_{-n}$. In FIG. 15, numeral 10 designates a predetermined section measured by a single photodiode 6, and 11 designates light which is projected from the fluorescent lamps 4, is reflected by the predetermined section 10, passes through the aperture 9 of the stopping plate 8, and is incident on the photodiode 6.

In general, light reflectivity of an offset printing plate in a picture part is different from that in a non-picture part. The apparatus makes use of this characteristic. That is, by illuminating predetermined sections 10 in the printing plate 1 with the light of the fluorescent lamps 4, the ink pattern area is measured based on the amount of light reflected by the predetermined sections 10.

In the apparatus, the light 11 projected from the fluorescent lamps 4 is reflected by the respective predetermined sections $10_{-1}$ to $10_{-n}$ in the printing plate 1, where the light is decayed according to the reflectivity thereof, and thereafter the light passes through the apertures $9_{-1}$ to $9_{-n}$ of the stopping plate 8 and is incident on the photodiodes $6_{-1}$ to $6_{-n}$. Since the photodiodes $6_{-1}$ to $6_{-n}$ are arranged linearly in the main scanning direction X, a strip-like region extending in the main scanning direction X is measured at one time. Thus, each strip-like region extending in the main scanning direction X is measured in series, while the measuring head consisting of the light source unit 2 and the light detecting unit 3 travels in a sub-scanning direction Y which is perpendicular to the main scanning direction X, thereby the ink pattern area of the whole printing plate 1 can be measured.

In the conventional apparatus as above mentioned, however, the predetermined sections 10 to be measured are determined by the shapes and positional relations of the apertures 9 of the stopping plate 8 and the effective photosensitive surfaces of the photodiodes 6. A problem is that errors in the shapes and positions thereof affect measuring accuracy directly.

The stopping plate 8 with an error of several $\mu$m to tens of $\mu$m can be manufactured by means of high-accuracy mechanical working, etching, laser cutting and the like. The effective photosensitive surfaces of the photodiodes 6 can be shaped with high accuracy by the technique of IC manufacture. However, the dimensional error in the shape of a package of photodiodes 6 is quite large, that is, about hundreds of $\mu$m in common. It is quite difficult to align tens of such photodiodes 6 with accuracy. Either the rotation or the inclination of a square element surface of each photodiode 6 affects the shape of the predetermined sections 10 to be measured. In the apparatus having such a structure, it has been difficult to achieve the high-accuracy measurement.

In the conventional apparatus as above mentioned, the predetermined sections $10_{-1}$ to $10_{-n}$ measured by the respective photodiodes $6_{-1}$ to $6_{-n}$ are divided so that the overlap of the predetermined sections 10 measured by the adjacent photodiodes 6 is as small as possible. When the predetermined sections $10_{-1}$ to $10_{-n}$ measured by the respective photodiodes $6_{-1}$ to $6_{-n}$ are out of position or out of shape with the production of a manufacturing error of optical parts, a dead area in the predetermined sections to be measured and an extremely high sensitivity region are liable to be generated. Particularly the dead area in the predetermined sections to be measured results in a failure in reading a line. In printing, ink must be supplied to a region having a picture part which includes only a single line. The failure in reading a line is more problematic than the error in the absolute value of a measured value and is a considerably serious problem particularly in printing of printed matter with a small ink pattern area such as business forms and the like.

When the apparatus is designed to reduce the overlapping part of sensitivities as the conventional apparatus, the effective photosensitive area of the photodiodes 6 is decreased. Accordingly, the amount of light which is incident on the photodiodes 6 is decreased, and a disadvantage is that the apparatus is subject to the influence of electric noises.

When the overlapping part of the sensitivities of the adjacent photodiodes 6 is small, the influence of a manufacturing error and assembling error of the parts on the measuring error is large in not a few cases.

In such an apparatus, it has been difficult to sufficiently achieve the intention of the ink pattern area meter.

SUMMARY OF THE INVENTION

The present invention is directed to an image reader for measuring light reflectivity or transparency of a predetermined section in an image bearing member.

A primary object of the present invention is to provide an image reader in which an error in the mounting position of photosensitive elements does not affect a measuring error.

Another object of the present invention is to provide an image reader which is capable of generating no dead area in predetermined sections to be measured and which is capable of detecting a large amount of light by photosensitive elements.

An image reader according to the present invention comprises a supporting means for supporting the image bearing member; a light source for illuminating the predetermined section to be measured in the image bearing member; a plurality of photosensitive elements one- or two-dimensionally arranged substantially in parallel with the image bearing member; a first stopping plate disposed between the photosensitive elements and the image bearing member and provided with apertures at positions corresponding to the photosensitive elements; a second stopping plate disposed between the photosensitive elements and the first stopping plate and provided with apertures which are in size within photosensitive surfaces of the photosensitive elements at positions corresponding to the photosensitive elements; and a computation means for finding an average light reflectivity or transparency of the predetermined section based on the output signal of the corresponding photosensitive elements.

In this case, when an effective distance between the photosensitive surfaces of the photosensitive elements and the apertures of the second stopping plate is designated by $S'$, an effective distance between the apertures of the second stopping plate and the apertures of the first stopping plate is designated by $S$, an effective dimension of the apertures of the first stopping plate is designated by $C_u$, an effective dimension of the apertures of the second stopping plate is designated by $C_l$, and an effective dimension of the photosensitive surfaces of the photosensitive elements is designated by $C_p$, the image reader satisfies the following conditional expression:

$$S' < \frac{C_p - C_l}{C_u + C_l} S \qquad (1)$$

When the expression (1) is satisfied, a slight deviation of the mounting position of the photosensitive elements does not affect the measuring error. That is, as far as the apertures of the second stopping plate are in size within the photosensitive surfaces of the photosensitive elements, the whole light directed from the predetermined sections in the image bearing member which are measured by the photosensitive elements through the apertures of the first stopping plate to the apertures of the second stopping plate is incident on the photosensitive elements.

Preferably, when a distance between centers of adjacent apertures of the second stopping plate is designated by p and an effective distance between the apertures of the second stopping plate and the image bearing member is designated by H, an overlapping factor F of the predetermined sections which are measured by adjacent photosensitive elements, which overlapping factor F is determined by the following expression (2), exceeds 0.1, and a flat factor J of sensitivity of the predetermined section to be measured, which flat factor J is determined by the following expression (3), is more than 0.95 and less than 1.05:

$$F = \frac{(p - C_u) \cdot C_l}{p \cdot C_u} \qquad (2)$$

$$J = \frac{S \cdot p}{H \cdot C_u} \qquad (3)$$

When the expressions (2) and (3) satisfy the above-mentioned conditions, the predetermined sections measured by the adjacent photosensitive elements overlap in sufficient part. Therefore, even if the position or shape of the predetermined sections measured by the respective photosensitive elements are different from the proper position or shape, the overlap of the adjacent predetermined sections to be measured is ensured so that no dead area is generated in the predetermined sections to be measured. The amount of incident light on the photosensitive elements can be increased, so that the influence of noise is easily reduced. When the expression (3) satisfies the above-mentioned condition, the composition of the sensitivities in the overlapping part of the predetermined sections measured by the adjacent photosensitive elements are substantially equal to the sensitivity in the non-overlapping part thereof, resulting in a substantially horizontal comprehensive sensitivity of the photosensitive elements on the image bearing member except at both ends thereof.

In the present invention, the image bearing member includes pictured paper, printing plates for offset printing and letterpress printing, original films produced in photolithography and the like.

The supporting means includes flat plates such as glass plates capable of placing thereon the image bearing member. In the image reader which measures light transparency, at least the portions of the supporting means which correspond to the predetermined sections to be measured in the image bearing member are required to be made of transparent material.

The light source is desired to emit light with stable intensity, for example, fluorescent lamps, LEDs, halogen lamps and incandescent lamps. In the present invention, a particular one of these need not be preferably used, and any of them will do.

The photosensitive elements include photodiodes, phototransistors, photoconductive. elements, charge coupled devices, phototubes and the like. The most preferable is photodiodes, which can generally output an excellent linearity characteristic while light is inputted thereto.

The two-dimensional arrangement of the photosensitive elements accords with the shape of the image bearing member. Printed matter is normally rectangular, and accordingly the photosensitive elements are arranged preferably in a rectangular matrix for versatility. It is, however, preferable to arrange the photosensitive elements concentrically where the image bearing member is limited to a circle. In the two-dimensional arrangement, the need for scanning is eliminated when the image bearing member is sufficiently small, thereby the time required for measurement is shortened. In the case where the photosensitive elements cannot be arranged two-dimensionally due to the restrictions by the space in which the elements are arranged and the number of elements, the photosensitive elements are arranged in one or two rows, i.e., one-dimensionally, to scan and measure the image bearing member in the direction perpendicular to the arrangement direction. In such a case, normally, the photosensitive elements are equally spaced in one or two rows. Particularly when the photosensitive elements are large relative to spatial resolution, a zigzag arrangement is preferable. In the one-dimensional arrangement, the need for scanning often occurs, however, the space in which the photosensitive elements and accompanying circuit elements are disposed is not subject to restriction, so that the spatial resolution is easily improved. Furthermore, since the measurement with a smaller number of photosensitive elements in a wider range is attainable, costs are easily reduced.

Preferably, the first and second stopping plates are manufactured by high-accuracy mechanical working or by a processing method in which a particularly high accuracy is expected such as laser cutting or etching while being formed as thinly as possible. For example, in order to provide a measuring error of 1% or less with the spatial resolution of 10 mm, the manufacturing accuracy of each part of the stopping plates is desired to be 10 μm or less. Preferably, each of the first and second stopping plates is formed of a plate provided with apertures at positions corresponding to the respective photosensitive elements. In such a structure, the number of parts is decreased and the positional relation between the apertures is easily maintained with accuracy. The shape of the apertures is in common square or rectangular. However, there is no particular problem if the apertures may be parallelogrammatic, trapezoidal, triangular or hexagonal. As for the position of the second stopping plate, the distance from the photosensitive elements is preferably as short as possible because the size of the photosensitive elements can be accordingly decreased. It is further preferable to employ the first and second stopping plates having the same design in light of measuring accuracy.

The computation means is a means for executing various signal conversions, operations and the like in order to find an ink pattern area rate of the image bearing member based on output signals of the respective photosensitive elements. For example, in the application to an ink pattern area meter for printing, it is adaptable to divide the image bearing member into strip-like small regions (hereinafter referred to as strips) and to find the ink pattern area rate for each strip by the computation means. In this case, the values measured at respective measuring points included in a single strip region must be normally added up. A means for the adding-up process is also included in the computation means.

The image reader preferably further comprises a shading correction means for correcting sensitivity and offset variations of each measuring set. A measuring set is a set of components, from the light source to an electric circuit, related to the measurement of the predetermined section by a single photosensitive element. Illumination unevenness of the light source and sensitivity unevenness of the photosensitive elements are corrected for by the shading correction means so that the measuring accuracy of the ink pattern area rate can be improved. The shading correction is not necessarily required to be executed on all of the measuring sets corresponding to the respective photosensitive elements, but may be executed only on some measuring sets. The correction may be carried out such that some measuring sets are integrated into a measuring set group and the average value of the measured results by the measuring set group is made to coincide with that by another measuring set group.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
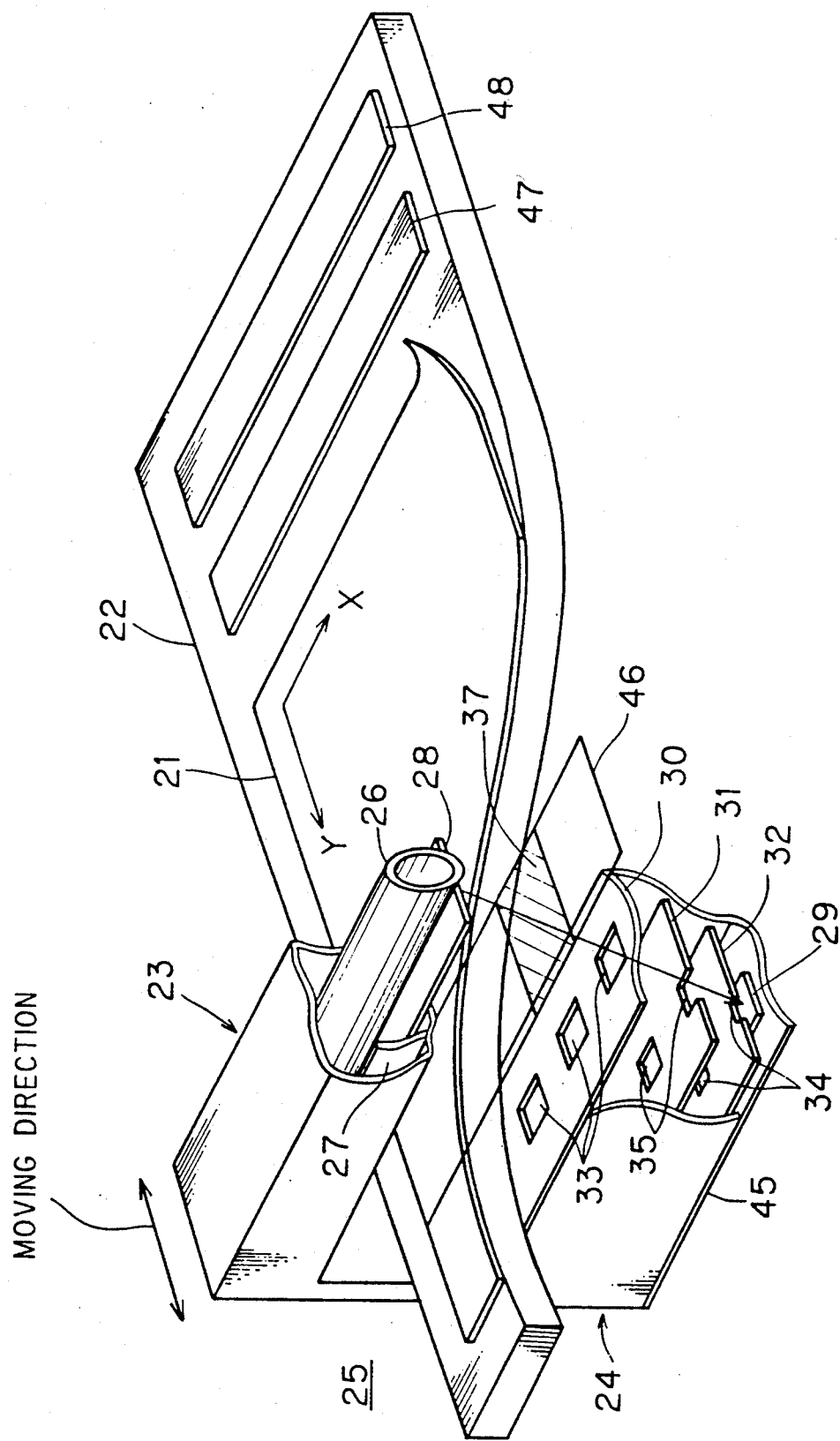
FIG. 1 is a perspective view of an image reader according to an embodiment of the present invention.

Referring to the drawings, a preferred embodiment of the present invention is described in detail hereinafter.

Figure 2:
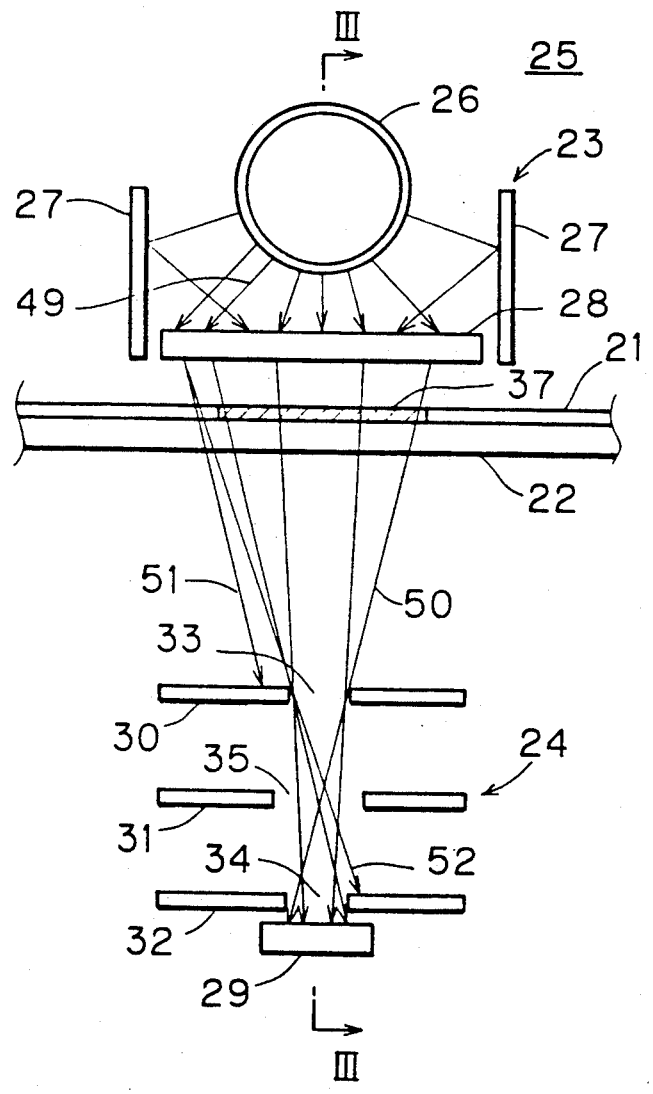
FIG. 2 is a cross-sectional view showing a major part of the apparatus shown in FIG. 1.
Figure 3:
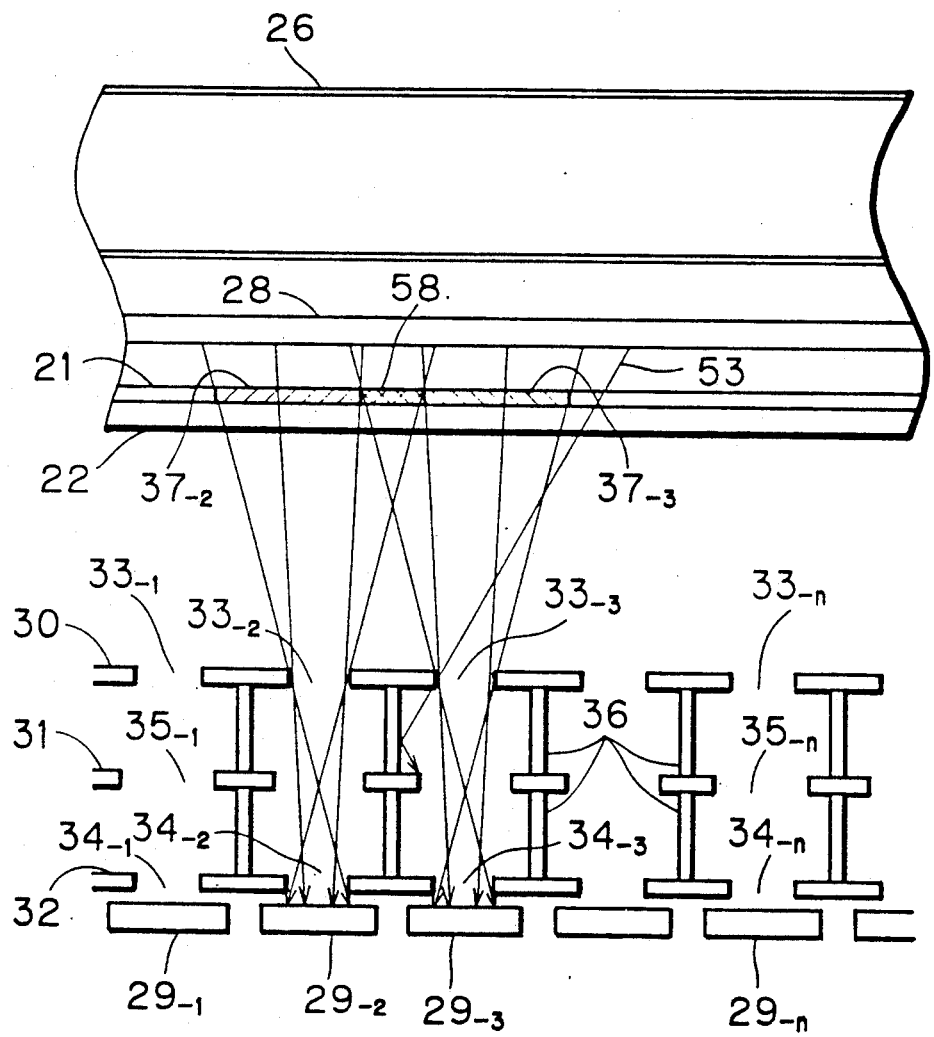
FIG. 3 is a cross-sectional view taken along the line III—III of FIG. 2.

The apparatus of the present invention is a light-transmission type image reader for measuring an ink pattern area rate of an original film for use in a prepress process of offset printing and the like. First, the structure of this apparatus is described referring to FIGS. 1 to 3. FIG. 1 is a perspective view of the apparatus. FIG. 2 is a cross-sectional view illustrating in detail an original film and a measuring head of FIG. 1. FIG. 3 is a cross-sectional view taken along the line III—III of FIG. 2.

As shown in FIGS. 1 to 3, the apparatus comprises a transparent film stand 22 for placing thereon an original film 21 such as PET which is an image bearing member, and a measuring head 25 comprising a light source unit 23 and a light detecting unit 24 and travelling in a sub-scanning direction Y with the film stand 22 between the light source 23 and the light detecting unit 24.

The light source unit 23 disposed over the upper side of the film stand 22 comprises a fluorescent lamp 26 extending in a main scanning direction X, reflecting plates 27 disposed on the both sides of the fluorescent lamp 26, and a diffusion desk 28 disposed between both the reflecting plates 27 under the fluorescent lamp 26.

The light detecting unit 24 disposed below the lower side of the film stand 22 comprises a multiplicity of photodiodes $29_{-1}$ to $29_{-n}$ arranged in a line in the main scanning direction X on a plane parallel to the film stand 22, a first stopping plate 30, a middle stopping plate 31 and a second stopping plate 32 all of which are disposed between the photodiodes 29 and the film stand 22.

The first stopping plate 30 is disposed between the film stand 22 and the photodiodes 29 and is provided with apertures $33_{-1}$ to $33_{-n}$ at positions corresponding to the respective photodiodes $29_{-1}$ to $29_{-n}$.

The second stopping plate 32 is disposed close above the photodiodes $29_{-1}$ to $29_{-n}$ and is provided with apertures $34_{-1}$ to $34_{-n}$ which are smaller in size than the photosensitive surfaces of the photodiodes $29_{-1}$ to $29_{-n}$, and at positions corresponding to the respective photodiodes $29_{-1}$ to $29_{-n}$.

The middle stopping plate 31 is disposed between the first stopping plate 30 and the second stopping plate 32 and is provided with apertures 35, the dimension of which is larger than the dimensions of the apertures 33 and 34 at positions corresponding to the respective photodiodes $29_{-1}$ to $29_{-n}$. The first stopping plate 30, the middle stopping plate 31 and the second stopping plate 32 are coupled to each other by obstructors 36, as shown in FIG. 3, for partitioning the space between the first and second stopping plates 30 and 32 into portions corresponding to the photodiodes $29_{-1}$ to $29_{-n}$.

In FIG. 2, numeral 37 designates a predetermined section measured by a single photodiode 29 in the original film 21. Predetermined sections (e.g., $37_{-2}$ and $37_{-3}$) measured by the adjacent photodiodes (e.g., $29_{-2}$ and $29_{-3}$) are designed to overlap partially (e.g., a region 58), as shown in FIG. 3.

Figure 4:
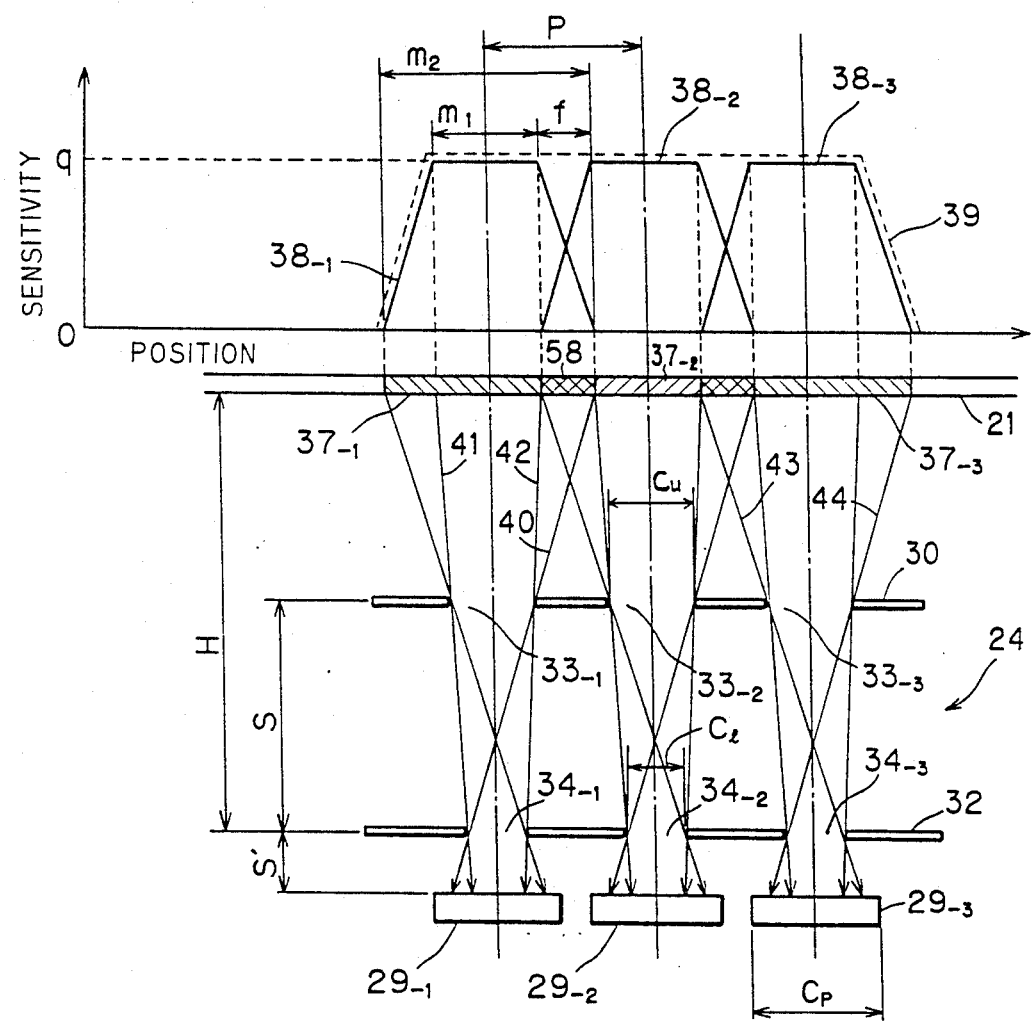
FIG. 4 is a schematic view showing the relation between a light detecting unit and sensitivity of each measuring set.

FIG. 4 is a schematic view showing the relation between the light detecting unit 24 structured as mentioned above and sensitivities $38_{-1}$ to $38_{-3}$ of the respective photodiodes $29_{-1}$ to $29_{-3}$ on the original film 21. As is recognized from FIG. 4, the sensitivities $38_{-1}$ to $38_{-3}$ of the respective photodiodes $29_{-1}$ to $29_{-3}$ show a substantially trapezoidal characteristic. The reference character $m_2$ designates the length of the lower base of the trapezoid indicative of the sensitivity 38, $m_1$ designates the length of the upper base thereof, f designates the length of an inclined side thereof in the main scanning direction X, and p designates the distance between the centers of the adjacent photodiodes 29.

In FIG. 4, reference character S' designates an effective distance between the photosensitive surfaces of the photodiodes 29 and the apertures 34 of the second stopping plate 32, S designates an effective distance between the apertures 34 of the second stopping plate 32 and the apertures 33 of the first stopping plate 30, H designates an effective distance between the second stopping plate 32 and the predetermined sections to be measured in the original film 21, $C_u$ designates an effective dimension of the apertures 33 of the first stopping plate 30, $C_l$ designates an effective dimension of the apertures 34 of the second stopping plate 32, and $C_p$ designates an effective dimension of the photosensitive surfaces of the photodiodes 29.

A plane is now supposed which includes the direction in which the photodiodes $29_{-1}$ to $29_{-3}$ are arranged and a straight line connecting the geometrical center of the sensitivity 38 of the predetermined section 37 measured by a single photodiode 29 on the original film 21 and the center of the corresponding aperture 34 of the second stopping plate 32. The effective dimensions $C_u$ and $C_l$ are the lengths of line segments in which the plane intersects the corresponding apertures 33 and 34 of the stopping plates 30 and 32, respectively. The effective dimension $C_p$ is the length of a line segment in which the plane intersects the photosensitive surface of the corresponding photodiode 29. For example, when the shapes of the apertures 33 of the first stopping plate 30 and the apertures 34 of the second stopping plate 32 are rectangular or parallelogrammatic, the effective dimensions are the length of one side of the rectangle or parallelogram. When the shapes are trapezoidal, the effective dimensions are the average length of the upper and lower bases of the trapezoid. When the shapes are triangular, the effective dimensions are the half length of the base of the triangle. A hexagon is treated as a combination of two trapezoids. When material with a refraction index different from air, such as glass, is present between the original film 21 and the photosensitive surfaces of the photodiodes 29, an optical path length is changed by the effect of the refraction. This effect should be taken into account to find the effective distances S', S and H.

For example, when the thickness of the film stand 22 is d' and the refraction index of it is n, the effective distance H is the same as the geometrical distance between the center of the predetermined section and the center of the corresponding aperture 34 of the second stopping plate 32 where the film stand 22 is exchanged with an air layer with a thickness d/n.

To be more concrete, we may show the following example: For the case where the center of the predetermined section is disposed right over the center of the aperture 34 of the second stopping plate 32 and the geometrical distance between the two centers is 100 mm, and n is equal to 1.5, and d is equal to 30 mm, the effective distance H is reduced to 90 mm.

Similar discussions are also valid for S and S'. When no material with a different refraction index is interposed, the effective distances are geometrical distances.

In this apparatus, the dimensions of the respective elements defined in this manner are set to satisfy the following expression (1):

$$S' < \frac{C_p - C_l}{C_u + C_l} S \tag{1}$$

where $C_p > C_l$.

In this apparatus, an overlapping factor F of the predetermined sections 37 measured by the adjacent photodiodes 29, which factor is found by the following expression (2), is set to exceed 0.1. A flat factor J of the sensitivities 38 of the predetermined sections 37, which factor is found by the following expression (3), is set to be more than 0.95 and less than 1.05.

$$F = \frac{(p - C_u) \cdot C_l}{p \cdot C_u} \tag{2}$$

$$J = \frac{S \cdot p}{H \cdot C_u} \tag{3}$$

When the expression (1) is satisfied, the whole light directed from the predetermined sections 37 measured by the photodiodes 29 through the apertures 33 of the first stopping plate 30 to the apertures 34 of the second stopping plate 32 is incident on the photodiodes 29 without the influence of the error in the mounting position of the photodiodes 29, as far as the apertures 34 of the second stopping plate 32 are in size within the photosensitive surfaces of the photosensitive elements 29. When the expressions (2) and (3) satisfy the above-mentioned conditions, the sensitivities $38_{-1}$ to $38_{-3}$ of the respective photodiodes $29_{-1}$ to $29_{-3}$ overlap partially, and comprehensive sensitivity 39 can be formed to be horizontal except at the both ends thereof, as shown in FIG. 4.

The reason for this is examined hereinafter. For the formation of the horizontal comprehensive sensitivity 39, the requirements described below must be satisfied. As shown in FIG. 4, light 40 directed from the right end of one predetermined section $37_{-1}$ through the right end of the aperture $33_{-1}$ of the first stopping plate 30 is required to pass through the left end of the aperture $34_{-1}$ of the second stopping plate 32 and be incident on the photodiode $29_{-1}$. Light 41 directed from the position corresponding to the left end of the horizontal part of the sensitivity $38_{-1}$ in the same predetermined section $37_{-1}$ through the left end of the aperture $33_{-1}$ of the first stopping plate 30 is required to pass through the left end of the aperture $34_{-1}$ of the second stopping plate 32 and be incident on the photodiode $29_{-1}$. Light 42 directed from the position corresponding to the right end of the horizontal part of the sensitivity $38_{-1}$ in the same predetermined section $37_{-1}$ through the right end of the aperture $33_{-1}$ of the first stopping plate 30 is required to pass through the right end of the aperture $34_{-1}$ of the second stopping plate 32 and be incident on the photodiode $29_{-1}$.

Figure 5:
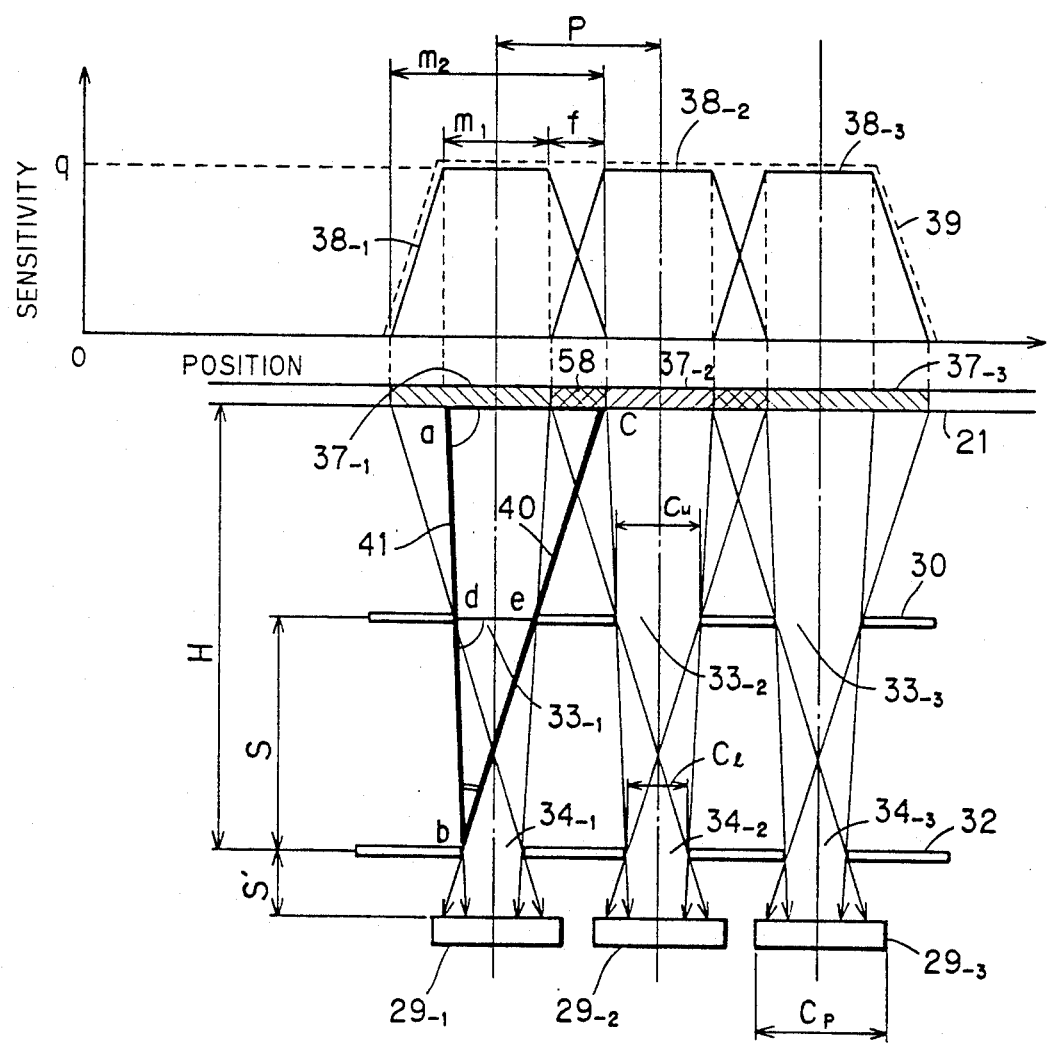
FIGS. 5 to 7 are views for explaining required conditional expressions, respectively.

In FIG. 5, two triangles $\triangle abc$ and $\triangle dbe$ related to the lights 40 and 41 are considered here. Since the triangles $\triangle abc$ and $\triangle dbe$ are similar figures of each other, the following equation (4) holds:

$$\frac{ac}{H} = \frac{de}{S} \tag{4}$$

When line segments $ac = m_1 + f$ and $de = C_u$ are substituted in the equation (4), the equation (5) is provided:

$$\frac{m_1 + f}{H} = \frac{C_u}{S} \tag{5}$$

On the other hand, the expression:

$$p = \frac{m_1}{2} + f + \frac{m_1}{2} = f + m_1$$

is substituted in the equation (5), and thereby the following equation (6) is provided:

$$\frac{S}{H} = \frac{C_u}{p} \tag{6}$$

This equation is a condition for the formation of the horizontal sensitivities of the predetermined sections to be measured. By a slight transformation of this equation, the flat factor J of the sensitivities of the predetermined sections to be measured is defined as follows:

$$J = \frac{S \cdot p}{H \cdot C_u} = 1$$

The equation (6) is derived theoretically on the supposition of ideal conditions. In practice, an error of about 5% is allowed. Accordingly, the following expression (7) should hold:

$$1.05 > J > 0.95 \tag{7}$$

It is, of course, preferably that the error is smaller, desirably 1% or less.

Figure 6:
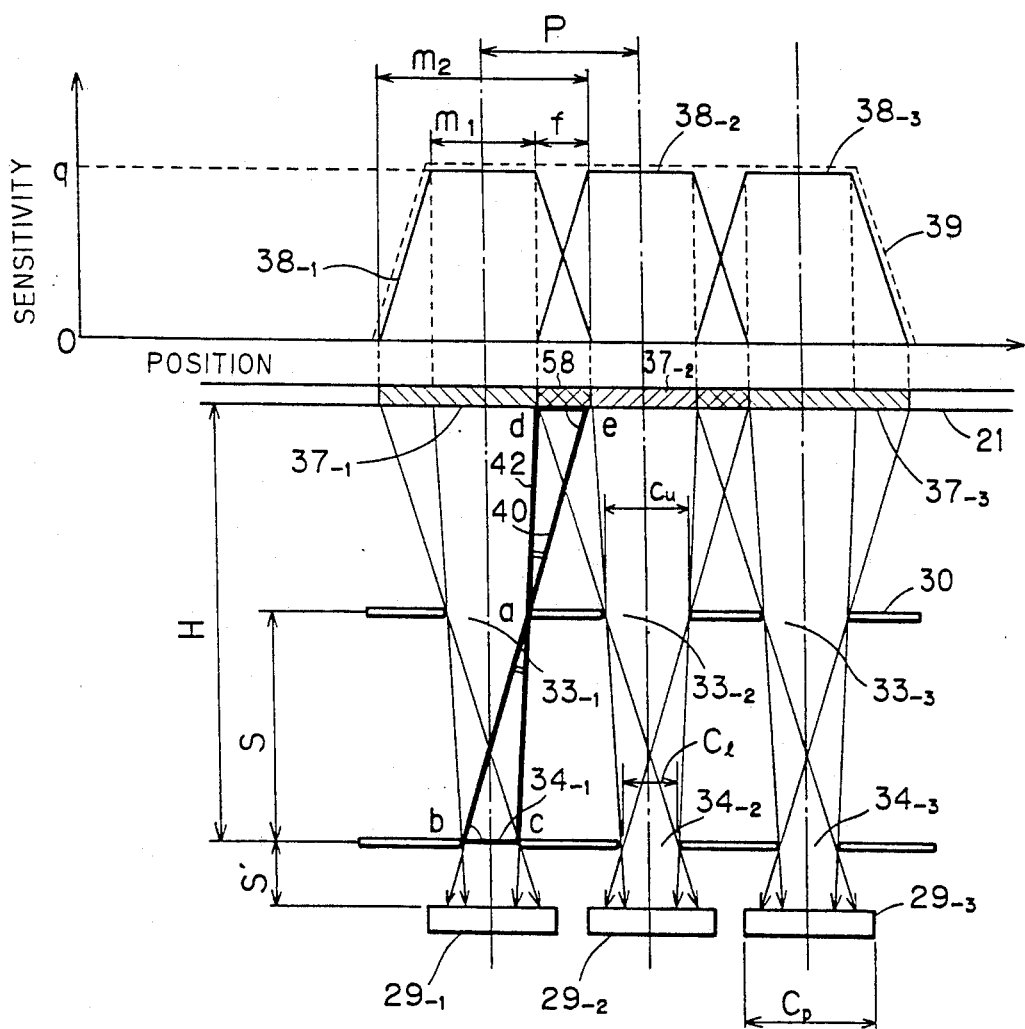

Next, in FIG. 6, two triangles $\triangle abc$ and $\triangle aed$ related to the lights 40 and 42 are considered. Since the triangles $\triangle abc$ and $\triangle aed$ are similar figures of each other, the following equation (8) holds:

$$\frac{de}{H - S} = \frac{bc}{S} \tag{8}$$

When line segments $de = f$ and $bc = C_l$ are substituted in the equation (8), the following equation is provided:

$$\frac{f}{H - S} = \frac{C_l}{S}$$

Accordingly the following equation (9) holds:

$$f = \left(\frac{H}{S} - 1\right) \cdot C_l \tag{9}$$

where $H > S$, as is apparent from FIG. 6.

The equation (9) can be expressed by means of the equation (6) as follows:

$$f = \left( \frac{p}{C_u} - 1 \right) C_l = \frac{p - C_u}{C_u} C_l$$

Therefore, the overlapping factor F is:

$$F = \frac{f}{p} = \frac{p - C_u}{p \cdot C_u} C_l \qquad (10)$$

The overlapping factor F should be large in order to restrict the occurrence of a dead area in the predetermined sections to be measured and an extremely high sensitivity region due to position shifts or deformations of the predetermined sections $37_{-1}$ through $37_{-3}$ measured by the individual photodiodes $29_{-1}$ through $29_{-3}$ with the production of a manufacturing error of optical parts. Unless the manufacturing error and the unevenness and warping of the image bearing member 21 are extremely large, the overlapping factor F of about 0.1 is sufficient, and that of 0.2 is more preferably. Therefore the following expression (11) is provided:

$$F > 0.1 \qquad (11)$$

When the expressions (7) and (11) are thus satisfied, the sensitivities $38_{-1}$ through $38_{-3}$ of the adjacent photodiodes $29_{-1}$ through $29_{-3}$ overlap partially, and the comprehensive sensitivity 39 is formed to be horizontal except at both ends thereof.

On the other hand, in order to enter the photodiodes 29 the whole light directed from the predetermined sections 37 to be measured by the photodiodes 29 through the apertures 33 of the first stopping plate 30 and the apertures 34 of the second stopping plate 32, the requirements described below must be satisfied. As shown in FIG. 4, light 43 directed from the left end of one predetermined section $37_{-3}$ through the left end of the aperture $33_{-3}$ of the first stopping plate 30 is required to pass through the right end of the aperture $34_{-3}$ of the second stopping plate 32 and be incident on the photodiode $29_{-3}$ within the photosensitive surface. Similarly, light 44 directed from the right end of the same predetermined section $37_{-3}$ through the right end of the aperture $33_{-3}$ of the first stopping plate 30 is required to pass through the left end of the aperture $34_{-3}$ of the second stopping plate 32 and be incident on the photodiode $29_{-3}$ within the photosensitive surface.

Figure 7:
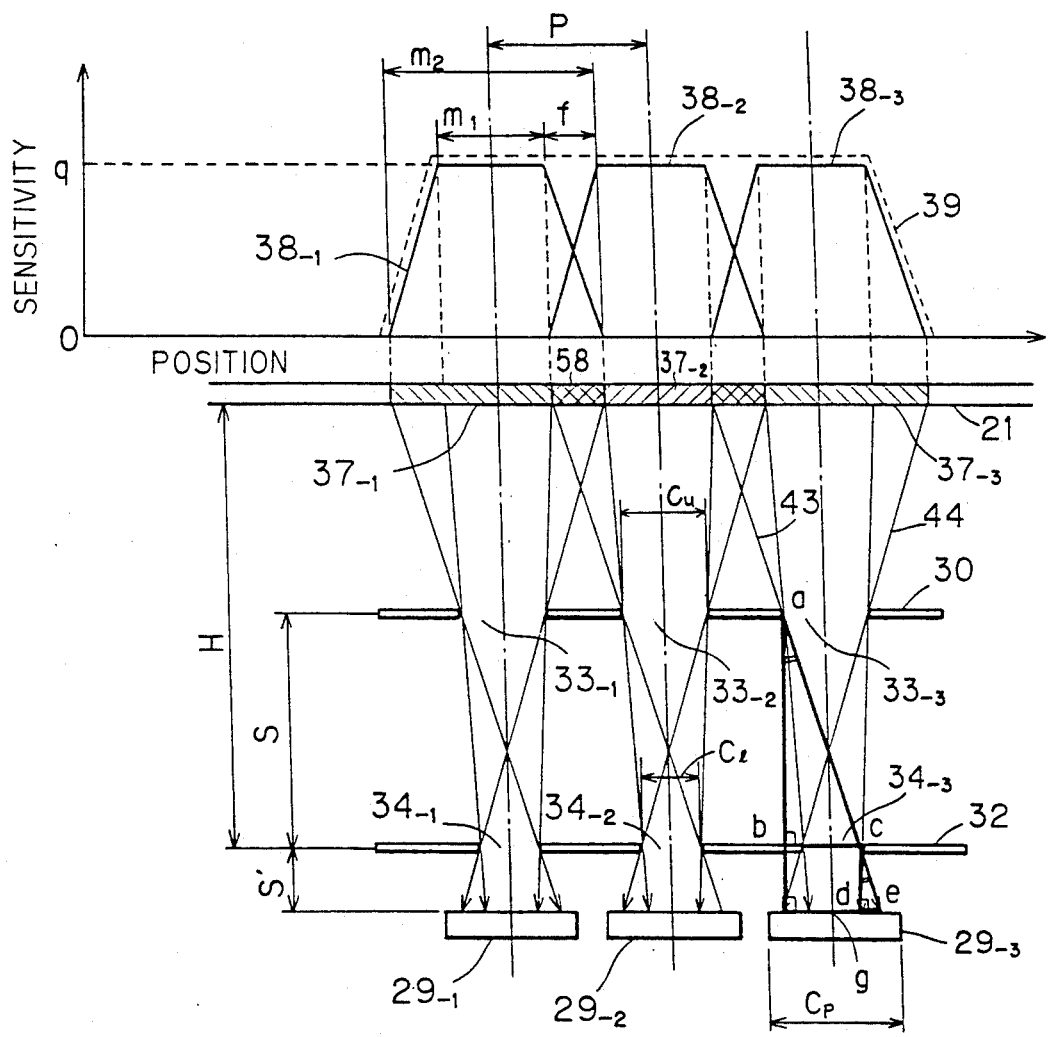

Because lights 43 and 44 are symmetrical with respect to the center line, we consider only light 43 and the two triangles $\Delta abc$ and $\Delta cde$ related to the light 43 as shown in FIG. 7. Points a, c and e are on the optical path of light 43, respectively. Line segments ab and cd are perpendicular to the photosensitive surfaces of the photodiodes 29, respectively. Since the triangles $\Delta abc$ and $\Delta cde$ are similar figures of each other, the following equation (12) holds:

$$\frac{ab}{bc} = \frac{dc}{de} \qquad (12)$$

An effective dimension $C_{p0}$ of the photosensitive surface of the photodiode $29_{-3}$ which is the limit of incidence of the light 43 on the photodiode $29_{-3}$ is two times longer than the distance between the point e and the center g of the photodiode $29_{-3}$ because of the symmetrical relation. ($C_{p0}$ expresses $C_p$ where an equality sign is substituted for the inequality sign in the expression (1).) Therefore, line segments bc and de are given by $(C_u/2)+(C_l/2)$ and $(C_{p0}/2)-(C_l/2)$, respectively.

The expressions $bc=(C_u/2)+(C_l/2)$, $ab=S$, $de=(C_{p0}/2)-(C_l/2)$, and $dc=S'$ are substituted in the equation (12), the following equation is provided:

$$\frac{S}{\frac{C_u}{2} - \frac{C_l}{2}} = \frac{S'}{\frac{C_{p0}}{2} - \frac{C_l}{2}}$$

Accordingly, the following equation (13) holds:

$$S' = \frac{C_{p0} - C_l}{C_u + C_l} S \qquad (13)$$

For effectively providing the lights 43 and 44 onto the photosensitive surfaces of the photodiodes 29 even in the case of the position shifts of the photodiodes 29, the photodiodes 29 should be disposed close to the second stopping plate 32. That is, the term S' on the left-hand side of the equation (13) should be smaller than the term on the right-hand side thereof. Thus, the expression (1):

$$S' < \frac{C_p - C_l}{C_u + C_l} S$$

is provided.

Next, in consideration of an error in practical mounting position, a manner of finding the value of S' which is desirable in design is discussed hereinafter. When the maximum positional deviation of the photodiodes 29 in the main scanning direction X is designated by $\pm \Delta c$, the range in which the presence of the photosensitive surfaces is ensured is indicated by the result of the subtraction of $2\Delta c$ from the effective dimension $C_p$ of the photodiodes 29. Accordingly the expression (1) is preferably as follows:

$$S' < \frac{C_p - 2\Delta c - C_l}{C_u + C_l} S \qquad (14)$$

where $C_p - 2\Delta c > C_l$ must hold.

On the other hand, a similar expression is provided with respect to the sub-scanning direction Y. In practical design, the smaller of the both maximum values of S' given from the two expressions with respect to the both directions must be selected.

It is supposed that the surfaces of the photodiodes 29 are inclined or that there is an error in height between the photodiodes 29 and a substrate 45 of the electric circuit. When the sum of these errors is designated by $\Delta S'$, S' must be smaller than the result of the subtraction of the sum $\Delta S'$ from the term on the right-hand side of the expression (14). To summarize the above, the following expression (15) is provided:

$$S' < \min\left\{ \frac{C_{px} - 2\Delta c_x - C_{lx}}{C_{ux} - C_{lx}} S, \frac{C_{py} - 2\Delta c_y - C_{ly}}{C_{uy} - C_{ly}} S \right\} - \Delta S' \qquad (15)$$

where $\min\{a, b\} = a \ (a < b)$
$\phantom{\text{where } \min\{a, b\} = } b \ (a > b)$ and $C_p$, $\Delta c$, $C_l$ and $C_u$ with subscripts x and y represent the respective values in the X and Y directions.

In practical design, there is no problem if S' is determined to satisfy the expression (15). Including changes with time and other factors such as rotation on the axis perpendicular to the photosensitive surfaces of the photodiodes 29, S' is preferably less than 0.9 times the value on the right-hand side of the expression (15). More preferably, S' is less than 0.5 times the value. If there is no problem in mechanical structure, the second stopping plate 32 is allowed to be in contact with the photodiodes 29 (S'=0). If a problem occurs such as the deformation of the second stopping plate 32 due to the contact, it is preferable to hold S' within the range larger than $\Delta S'$.

Next, consideration is given to the sensitivities where the flat factor J changes in the vicinity of 1. When a set of the elements S, p, H and $C_u$ satisfying J=1 is designated by $S_0$, $p_0$, $H_0$ and $C_{u0}$, the equation (6) is expressed by the following equation:

$$1 = \frac{S_0 \cdot p_0}{H_0 \cdot C_{u0}} \quad (16)$$

This is a standard design in the present invention. The equation (16) attains a value J which is not equal to 1 (for example, 0.9) when one of the following conditions is satisfied: S (or p) is J times $S_0$ (or $p_0$) while the elements remain unchanged; H (or $C_u$) is 1/J times $H_0$ (or $C_{u0}$) similarly; and the combination of the elements produces J times the value on the right-hand side of the equation (16) as a whole.

For simplification, it is supposed that p is equal to $J \cdot p_0$. Substantially similar results can be provided in the other cases. The change in the distance between the photodiodes 29 from $p_0$ to p $(=J \cdot p_0)$ has the same meaning as the translation of the trapezoidal sensitivities 38 of the respective photodiodes 29 in FIG. 5 by $\Delta p = p - p_0$. The comprehensive sensitivity 39 where the distance has been changed is shown in FIGS. 8A through 8D according to the conditions of J, f and $\Delta p$. FIGS. 8A through 8D show the comprehensive sensitivity 39 where $J<1$ and $f>\Delta p$, where $J>1$ and $f>\Delta p$, where $J<1$ and $f<\Delta p$, and where $J>1$ and $f<\Delta p$, respectively. As shown in FIGS. 8A through 8D, abnormal parts are generated in which the sensitivity changes by $\Delta q$ from the ideal comprehensive sensitivity, when p is multiplied by J $(\approx 1)$.

Figure 8A:
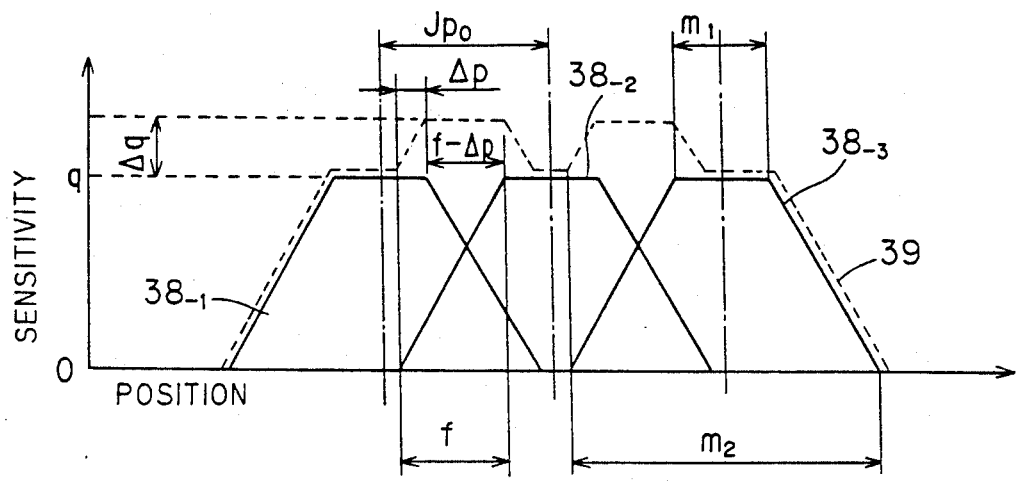
FIGS. 8A, 8B, 8C and 8D show the sensitivities where a flat factor J changes in the vicinity of 1, respectively.
Figure 8B:
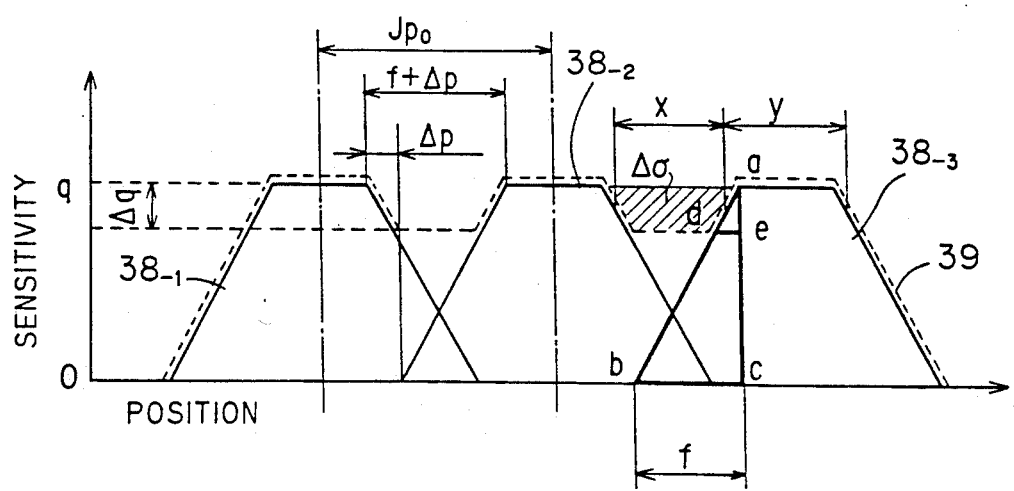

The proportion of the deviation $\Delta q$ to the sensitivity q of the comprehensive sensitivity 39 in a horizotal part, that is, a rate of sensitivity change r is found hereinafter. First, the rate at $f>\Delta p$ is considered as shown in FIGS. 8A and 8B. From the similar relation between $\triangle abc$ and $\triangle ade$ shown in FIG. 8B, the following equation (17) is provided:

$$\Delta q = \frac{q \cdot \Delta p}{f} \quad (17)$$

Therefore the rate of sensitivity change r can be expressed by the use of the equations (10) and (17) as follows:

$$r = \frac{\Delta q}{q} = \frac{\Delta p}{f} = \frac{\Delta p}{p \cdot F} = \frac{1 - J}{F} \quad (18)$$

As is apparent from FIGS. 8A and 8B, $\Delta q < q$ holds when $f > \Delta p$.

Figure 8C:
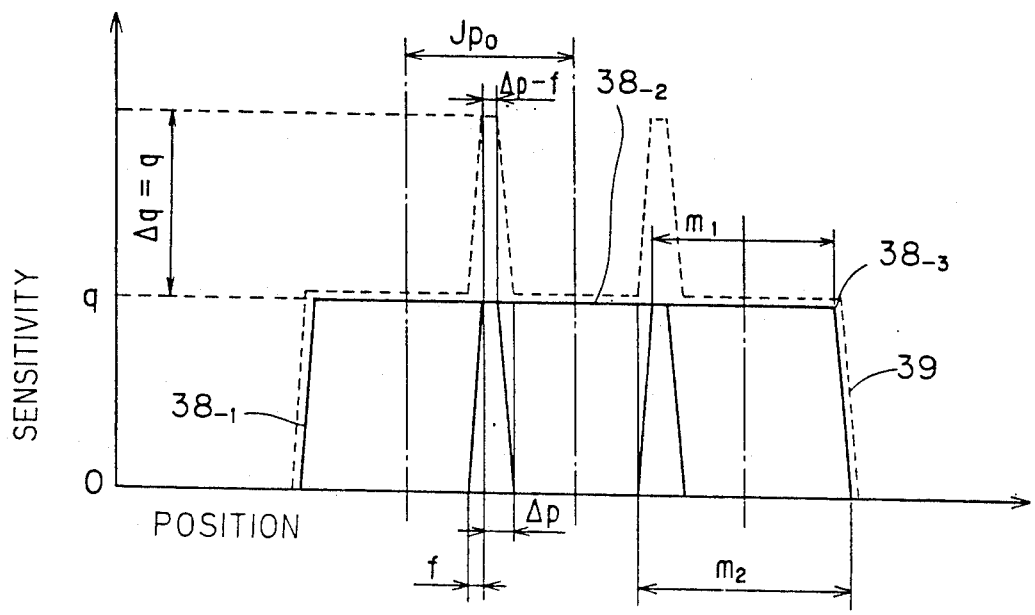
Figure 8D:
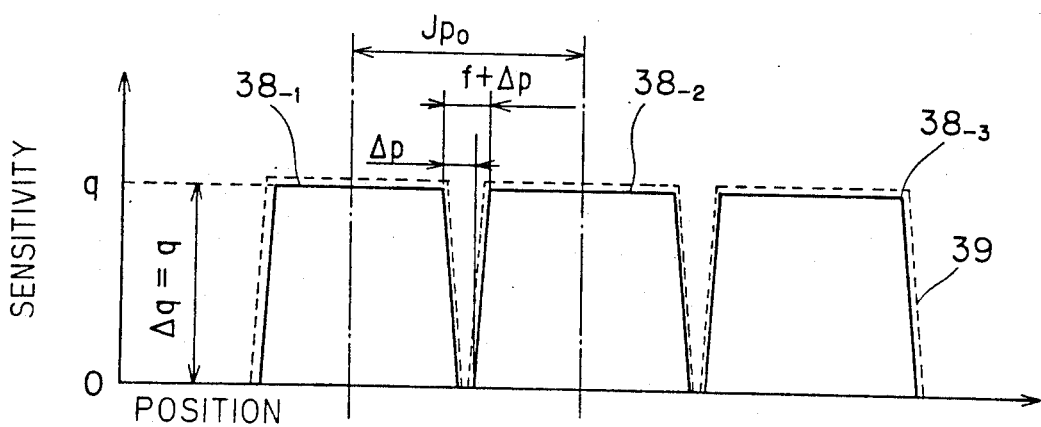

On the other hand, $\Delta q = q$ holds when $f < \Delta p$, as shown in FIGS. 8C and 8D. The rate of sensitivity change r is 1 from the expression (18). Regions having twofold sensitivity are generated when $J<1$, as shown in FIG. 8C. On the other hand, regions having sensitivity of zero are generated when $J>1$, as shown in FIG. 8D, where ink patterns are completely disregarded.

In fact, such sensitivity abnormality occurs in the range of f when $\Delta p > f$ and in the range of $\Delta p$ when $\Delta p < f$. General sensitivity change, that is, a measuring error can be evaluated by a ratio R expressed by the following equation:

$$R = \frac{\Delta \sigma}{\sigma}$$

where $\Delta \sigma$ is the amount of sensitivity change in the abnormal part x (e.g., the area of the hatched region of FIG. 8B), and $\sigma$ is the area within the sensitivity profile 38 of a single photodiode 29. Independently of the relation between f and $\Delta p$, the ratio R is given from FIG. 5 by the following expression:

$$R = \frac{\Delta \sigma}{\sigma} = \frac{\Delta p}{p} = 1 - J$$

Figure 9:
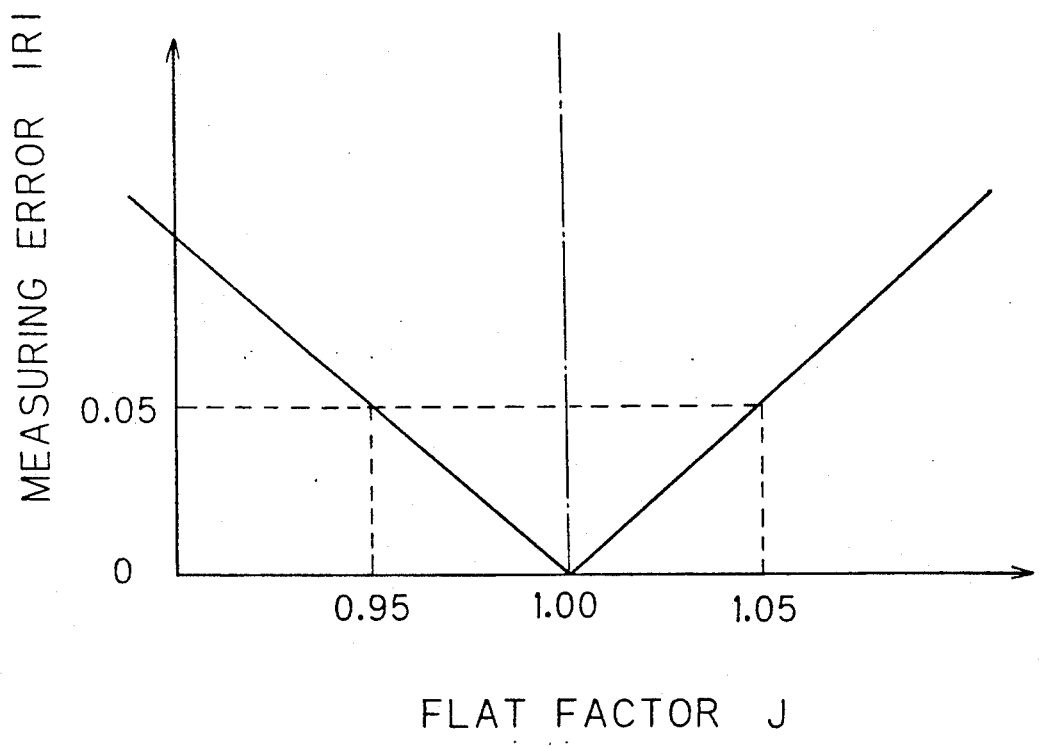
FIG. 9 shows the relation between the flat factor J and a measuring error.

FIG. 9 is a graph on which the absolute values of the ratios R related to the measuring error are plotted as a function of J derived from the above discussion.

In general, the ink pattern area meter is not allowed to produce a measuring error of more than 5%. Hence, J must be within the range of 0.95 to 1.05. For securely measuring the ink pattern with a low ink pattern area rate (e.g., about 5 to 15% in average in business forms and the like), in which J particularly has a large influence, J is preferably within the range of 0.99 to 1.01. In the present invention, the flat factor J of the sensitivities is designed to be 1.

Next, the overlapping factor F is examined. In the above discussion, it is described that the area ratio R in the sensitivity abnormal part x is independent of the length f. The rate of sensitivity change r in the sensitivity abnormal part x is inversely proportional to the overlapping factor F. When a fine line is present in the sensitivity abnormal part x where the real flat factor J of the apparatus is deviated from 1 due to a manufacturing error of the apparatus or a contact failure to the film stand 22 and unevenness of the image bearing member 21, an error in the measured ink pattern area rate of the line is increased as the overlapping factor F is decreased. Particularly when $f < \Delta p$, the measured ink pattern area rate in the sensitivity abnormal part x is either twice larger than the correct value or not recognized in the least.

As for the ink patterns which have low total ink pattern area rates (5 to 15%) and include a large number of lines such as lettered originals and business forms, in general, some of them (e.g., the ink patterns with an ink pattern area rate of less than 5%) are affected by the error when the deviation of the real flat factor J of the apparatus from 1 exceeds 0.01, i.e., 1%. When the deviation exceeds 5%, the reliability of the measured ink pattern area rates in almost all of the ink patterns is problematic. The measuring error of 5% with the ink pattern area rate of 5% results in the error of 100% relatively. An ink pattern area meter with such an error cannot be practically used.

It is an extremely serious drawback of an ink pattern area meter for ink presetting that the ink pattern is not completely recognized even if the value of the error itself is small. This is because the smallest ink pattern cannot be printed without an ink supply.

When the overlapping factor F is 0.1 or more and the deviation of the flat factor J from 1 is 0.05 or less, $$r \leq 0.5$$

is obtained from the expression (18). Under this condition, any failure of recognition of the ink pattern does not occur at worst. More preferably, the overlapping factor F is 0.2 or more. In the preferred embodiment, the overlapping factor F is 0.6. By increasing the overlapping factor F, the rate of sensitivity change r in the sensitivity abnormal part x is decreased, so that the influence of the error can be restrained in the ink patterns with low ink pattern area rates.

It is preferable to increase the overlapping factor F in order to increase the amount of incident light on the photodiodes 29. The reason for this is described below.

First, it is supposed that the overlapping factor F is less than 1. When the distance p between the centers is constant, an increase in the overlapping factor F increases f. Because the line segment de=f from the equation (8), the larger f is, the larger the length of the line segment bc, i.e., $C_l$ is. Since the amount of incident light on the photodiodes 29 is proportional to $C_l$, the amount of incident light is increased in proportion to the increase in the overlapping factor F.

The proportionality of the amount of incident light on the photodiodes 29 to $C_l$ can be explained below. For example, light emitted from the center of the predetermined section $37_{-1}$ is incident only on the photodiode $29_{-1}$. The amount of the light is proportional to the length $C_l$ of one side of the aperture $34_{-1}$ of the second stopping plate 32. This is because the incident light on the photodiode $29_{-1}$ passes through the aperture $33_{-1}$ of the first stopping plate 30 only in the vicinity of the center thereof, thereby the amount of light is independent of the shape of the aperture $33_{-1}$. In the center of the predetermined section $37_{-1}$, the sensitivity $38_{-1}$ is horizontal as shown in FIG. 6 so that the sensitivity q of FIG. 6 is proportional to $C_l$. The amount of light in the horizontal part is the product of the length $m_1$ of the upper base of the trapezoidal sensitivity 38 and the sensitivity q. On the other hand, the amount of light in the non-horizontal part is as follows:

$$\tfrac{1}{2} \cdot f \cdot q \times 2 = f \cdot q$$

The incident light on the photodiode $29_{-1}$ is totally as follows:

$$m_1 \cdot q + f \cdot q = (m_1 + f) q = p \cdot q$$

and is found to be proportional to $C_l$ because of its proportionality to q.

The same is true for both the main scanning direction X and the sub-scanning direction Y. The incident light on the photodiodes 29 where the overlapping factor F in both directions is 0.2 is about four times larger than the incident light where the overlapping factor F is 0.1. The incident light where the overlapping factor F is 0.5 is about twenty-five times larger than the same. For increasing the amount of light, the overlapping factor F is preferably 0.2 or more, and more preferably 0.5 or more. However, when the overlapping factor F exceeds 1, the incident light on the photodiodes 29 is proportional to the length $C_u$ of one side of the apertures 33 of the first stopping plate 30. From the equation (2), it is found that the length $C_u$ of one side of the apertures 33 is decreased as the overlapping factor F is increased. As a result, the amount of incident light is decreased when the overlapping factor F exceeds 1.

It is found that the amount of incident light on the photodiodes 29 reaches the maximum at F=1 and is decreased as the overlapping factor F grows larger or smaller than 1. Therefore the overlapping factor F is preferably from about 0.5 to 2 from the standpoint of the increase in the amount of light.

Figure 10:
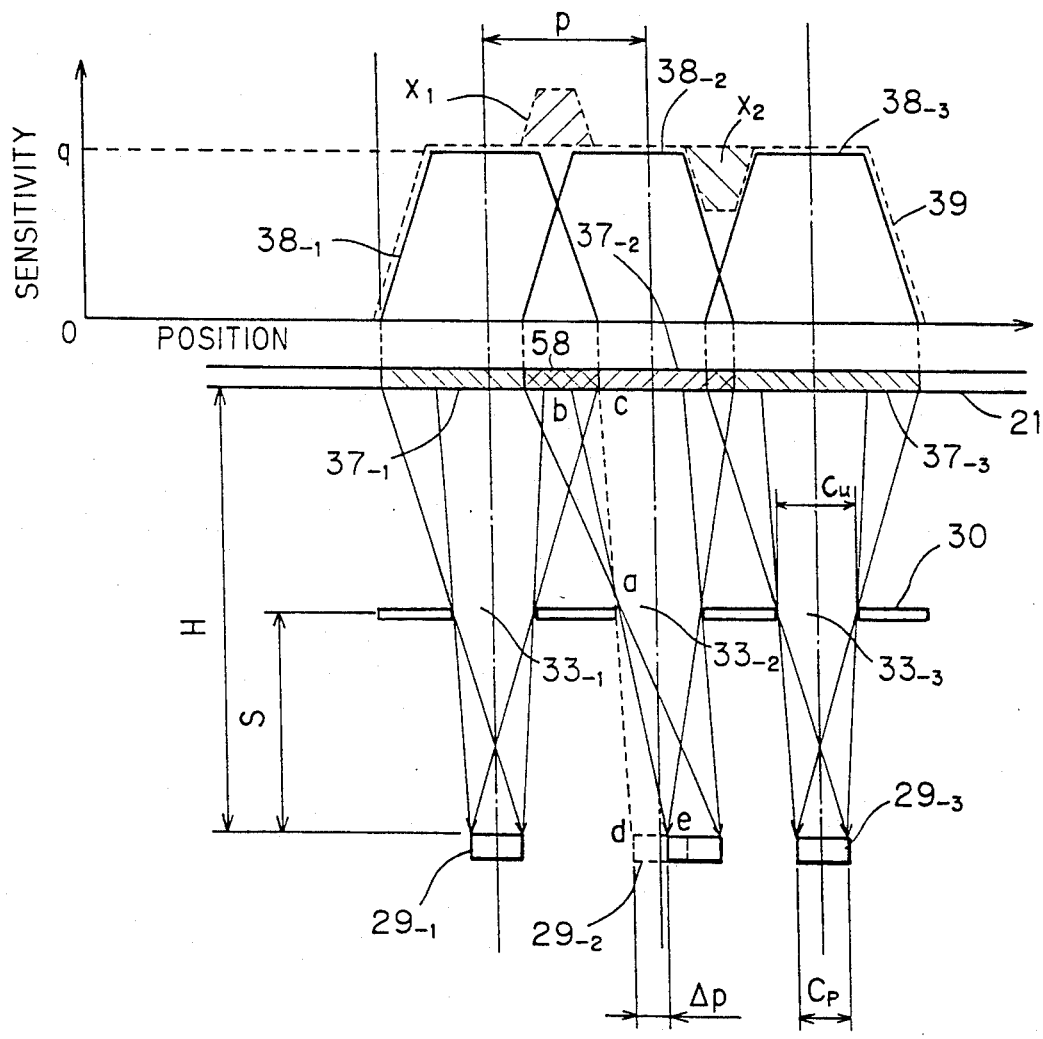
FIG. 10 shows the sensitivity where the position of a single photosensitive element is deviated.

Next, effects of the second stopping plate 32 are considered. For this purpose, influences of the position shifts of the photodiodes 29 in the absence of the second stopping plate 32 on the measuring error are first examined. FIG. 10 shows the sensitivity where the position of a single photodiode $29_{-2}$ is shifted by $\Delta p$. In FIG. 10, the sensitivity $38_{-2}$ of the photodiode $29_{-2}$ is translated by:

$$\Delta m = \frac{H - S}{S} \cdot \Delta p$$

because of the similar relation between $\Delta abc$ and $\Delta aed$. In this case, the comprehensive sensitivity 39 generates two abnormal parts $x_1$ and $x_2$. When the area of the abnormal part $x_1$ or $x_2$ is designated by $\Delta \sigma$, the ratio R of the area $\Delta \sigma$ to the area $\sigma$ of the sensitivity $38_{-2}$ is, similarly to the above discussion, as follows:

$$R = \frac{\Delta \sigma}{\sigma} = \frac{\Delta m}{p} = \frac{H - S}{S} \cdot \frac{\Delta p}{p}$$

The expressions (9) and (10) are substituted in this expression to obtain the following expression:

$$R = \frac{f \cdot \Delta p}{C_p \cdot p} = \frac{F}{C_p} \cdot \Delta p \qquad (19)$$

As is recognized from the expression (19), the ratio R is proportional to the overlapping factor F. For this reason, $\Delta p$ must be as small as possible when the overlapping factor F is large. As described above, the dimensional accuracy of the package of the photosensitive elements such as photodiodes and the mounting accuracy thereof are commonly about hundreds of $\mu m$. On the other hand, the processing accuracy of etching and the like is about several $\mu m$. Hence, a second stopping plate 32 provided with the apertures 34 which satisfy the expression (1) can reduce the influence of the position shifts of the photosensitive surfaces of the photodiodes 29 to about 1/100 or less. When the second stopping plate 32 is used, the expression (19) is as follows:

$$R = \frac{F}{C_l} \cdot \Delta p \qquad (20)$$

In the preferred embodiment, F=0.6, $C_l$=2 mm, $\Delta p$=0.003 mm and R=0.09%. Even if the elements in both the main scanning and sub-scanning directions are added, the error is held at 0.18%. When the second stopping plate 32 is not used, R is 18% even if $\Delta p$ =0.3 mm, as is not practical.

The second stopping plate 32 is unnecessary if the overlapping factor F could be zero. For setting the overlapping factor F to zero, according to the expression (2), it is required either to set $C_l$ (in this case, the effective dimension of the photosensitive surfaces of the photodiodes 29) to zero or to equalize p with $C_u$. It is however impossible to set the effective dimension of the photosensitive surfaces of the photodiodes 29 to zero. To satisfy $p = C_u$, the distance between the photodiodes 29 must be equalized with the effective dimension of the apertures 33 of the first stopping plate 30 from the expressions (8) and (9). As a result, adjacent apertures 33 overlap and no boundary part between the adjacent apertures 33 is formed. Furthermore, $p = C_u$ is equivalent to $H = S$, which has the same meaning as the contact of the first stopping plate 30 with the image bearing member 21. Such a structure is not attainable.

For comparison, it is supposed that the overlapping factor F is minimized in the absence of the second stopping plate 32. First, the value of $p - C_u$ is taken as 0.508 mm for approach to $p = C_u$. This is a width which is essential to provide the first stopping plate 30 with practical minimum rigidity. When the distance p between the photodiodes 29 and the effective dimension $C_p$ of the photosensitive surfaces of the photodiodes 29 are taken as 5.08 mm and 2 mm, respectively, which are the same values as in the preferred embodiment, the overlapping factor F is from the expression (2) as follows:

$$F = \frac{0.508}{5.08 \cdot (5.08 - 0.508)} \cdot 2 = 0.044$$

Both of this obtained value and $\Delta p = 0.3$ mm are substituted in the expression (19) and thereby R is as follows:

$$R = \frac{0.044}{2} \cdot 0.3 = 0.0066$$

The elements in both the main scanning and sub-scanning directions are added, and thereby the measuring error R becomes 1.32%. This is about seven times larger than the measuring error of the preferred embodiment. Only the positional error of the photosensitive surfaces of the photodiodes 29 accounts for a large part of the 5% measuring error in a required minimum ink pattern area rate. In general, the measuring error is preferably 1% or less for measurement of ink patterns with low ink pattern area rates in lettered originals, business forms or the like. This value, however, cannot be attained in this case. In addition, it is not easy to achieve $\Delta p = 0.3$ mm as an error including not only the dimensional error of the package but also the positioning error and the rotation and inclination of the photosensitive surfaces together. On the other hand, the measuring error R is 0.0132% when the overlapping factor F is 0.044 in the presence of the second stopping plate 32. This error can be completely disregarded.

The conclusion is that the second stopping plate 32 is effective for reduction in the measuring error where the overlapping factor F is very small and particularly more effective where the overlapping factor F is large for decreasing the rate of sensitivity change r in the sensitivity abnormal part x.

Referring again to FIG. 1, the light detecting unit 24 structured as mentioned above is provided with the respective photodiodes 29 mounted on the substrate 45 of the electric circuit in an arranged fashion in the main scanning direction X. The measuring set 25 measures an average light transparency of a strip 46 extending in the main scanning direction X substantially simultaneously through a multiplicity of photodiodes 29.

Two calibration strips 47 and 48 for shading correction are provided at an end of the film stand 22. The calibration strips 47 and 48 are made of the same material as the image bearing member 21 and composed of films with known ink pattern area rates, e.g., 0% and 100%.

Figure 11:
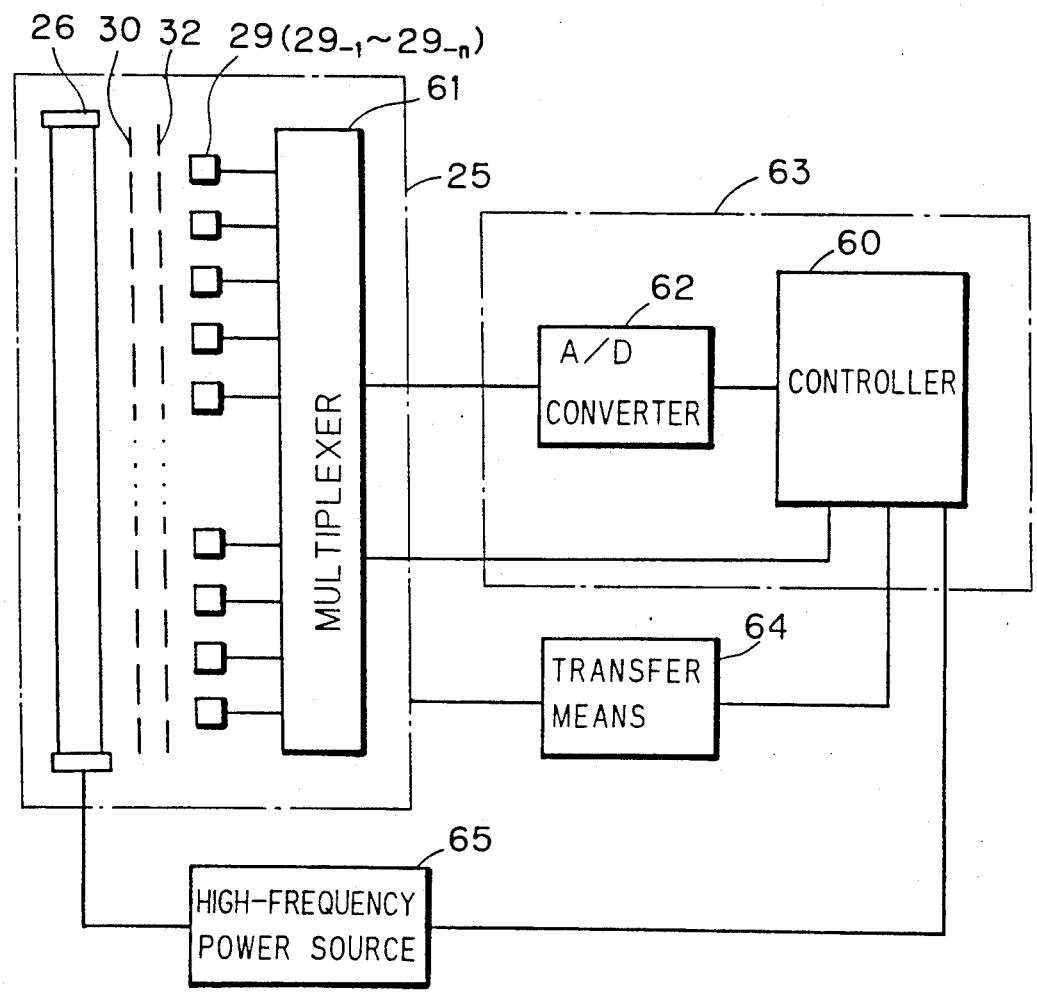
FIG. 11 is a block diagram showing the whole system of the embodiment of the present invention.

FIG. 11 is a block diagram showing the whole structure of the image reader according to the preferred embodiment of the present invention. As shown in FIG. 11, the measuring head 25 comprises the light source 26, the first stopping plate 30, the second stopping plate 32 and the photodiodes 29, as described above. The measuring head 25 further comprises a multiplexer 61 for selectively switching and outputting signals from the respective photodiodes $29_{-1}$ to $29_{-n}$ based on a control signal from a controller 60. A computation means 63 is formed with an A/D converter 62 for converting an analog output signal of the multiplexer 61 into a digital signal and a controller 60 connected to the A/D converter 62. The controller 60 includes a memory for storing the measured data of the respective photodiodes $29_{-1}$ to $29_{-n}$, and has functions of executing shading correction described later and calculating the ink pattern area rate by the use of the measured data.

The image reader further comprises a transfer means 64 for transferring the measuring head 25 in the sub-scanning direction relative to the image bearing member 21. The transfer means 64 is composed of well-known means which use, for example, a pulse motor and ball screws. The image reader further comprises a high-frequency power source 65 for operaing the fluorescent lamp 26. The transfer means 64 and the high-frequency power source 65 are driven respectively based on the control signal from the controller 60.

Figure 12:
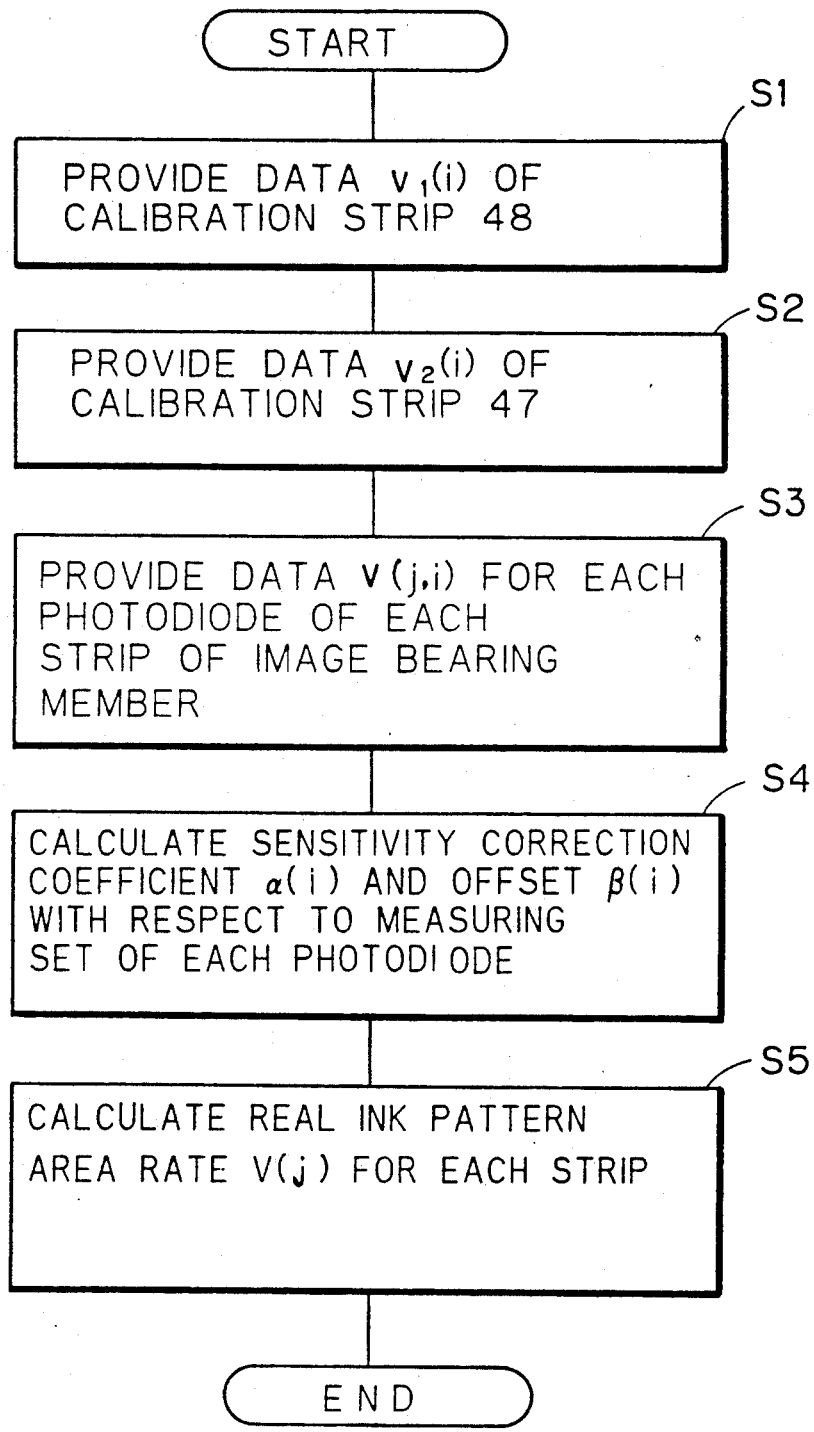
FIG. 12 is a flow chart showing the operation of the embodiment.

Next, the operation of the apparatus is described, referring to the flow chart of FIG. 12.

In consideration for the shading correction, predetermined ink pattern area rates $C_1$ and $C_2$ of the calibration strips 47 and 48 are stored previously in the memory of the controller 60.

In the initial state of the operation, the measuring head 25 stands ready on the outside of the region in which the image bearing member 21 such as an original film is placed (on the right-hand side of FIG. 1). On starting in measurement, the measuring head 25 is moved leftward in FIG. 1 to the calibration strip 48, at which the respective photodiodes $29_{-1}$ to $29_{-n}$ measure the light intensities of the corresponding regions. The measured data are transmitted through the multiplexer 61 and the A/D converter 62 to be stored in the memory of the controller 60 in series as data $v_1(i)$ ($i = 1$ to n) (process step S1 of FIG. 12).

Next, the measuring head 25 is moved to the calibration strip 47, at which the respective photodiodes $29_{-1}$ to $29_{-n}$ measure the light intensities of the corresponding regions similarly. Respective data $v_2(i)$ are stored in the memory of the controller 60 (process step S2).

Thereafter, the measuring head 25 is moved to the image bearing member 21. The whole section to be measured in the image bearing member 21 are divided into a multiplicity of (e.g., k-number of) strips 46. Every time the measuring head 25 reaches the center of each strip 46, the respective photodiodes $29_{-1}$ to $29_{-n}$ carry out the measurement for each strip. The measured data are stored in the memory of the controller 60 in series as data v(j,i) (j=1 to k and i=1 to n) (process step S3).

On finishing the measurement, the controller 60 performs the shading correction with use of the respective data to calculate a real ink pattern area rate. In detail, a sensitivity correction coefficient α(i) and an offset β(i) with respect to the measuring sets of the respective photodiodes 29 are found by the following expressions (process step S4):

$$\alpha(i) = \frac{C_1 - C_2}{v_1(i) - v_2(i)}$$

$$\beta(i) = \frac{C_2 v_1(i) - C_1 v_2(i)}{v_1(i) - v_2(i)}$$

Next, the real ink pattern area rate V(j) is found for each strip 46 according to the following expression (process step S5):

$$V(j) = \sum_{i=1}^{n} \{\alpha(i) \cdot v(j,i) + \beta(i)\}$$

On determining the real ink pattern area rates V(j) in this manner, the operation is terminated.

In this preferred embodiment, two calibration strips 47 and 48 are provided, thereby both the sensitivity and the offset are adjustable. For adjustment of only the sensitivity, it is sufficient to provide one calibration strip.

The operation of the measuring head 25 is described in detail hereinafter.

Referring to FIG. 2, light 49 emitted from the fluorescent lamp 26, after reflected from the reflecting plates 27 or directly without the reflection therefrom, illuminates the diffusion desk 28 to be once diffused therein. Diffused light 50 is decayed in the predetermined section 37 measured by a single photodiode 29 in the strip 46 of the original film 21 in accordance with the transparency thereof. The light 50 thereafter passes through the aperture 33 of the first stopping plate 30, the aperture 35 of the middle stopping plate 31 and the aperture 34 of the second stopping plate 32 to be incident on the photodiode 29.

Light 51 directed from the diffusion desk 28 through the vicinity of the predetermined section 37 (that is, not passing through the predetermined section 37) is blocked by the first stopping plate 30 so as not to be incident on the photodiode 29. Similarly, light 52 directed from the diffusion desk 28 through the vicinity of the predetermined section 37 (that is, not passing through the predetermined section 37) is blocked by the second stopping plate 32 so as not to be incident on the photodiode 29. In this fashion, the predetermined section 37 measured by the single photodiode 29 is determined by the apertures 33 and 34 of the first and second stopping plates 30 and 32. The dimensional relation of the respective reference characters defined in FIG. 4 are established to satisfy the expression (15):

$$S < \min\left\{\frac{C_{px} - 2\Delta c_x - C_{lx}}{C_{ux} - C_{lx}} S, \frac{C_{py} - 2\Delta c_y - C_{ly}}{C_{uy} - C_{ly}} S\right\} - \Delta S$$

Therefore, even if the photodiodes 29 are more or less out of position, the light directed from the predetermined sections 37 through the apertures 33 of the first stopping plate 30 to the apertures 34 of the second stopping plate 32 is incident on the photodiodes 29 effectively. Thus the error in the mounting position of the photodiodes 29 does not affect the measuring error.

The necessity for the photodiodes 29 to be arranged with accuracy is eliminated, as is useful for reduction of costs.

In this apparatus, the overlapping factor F of the predetermined sections 37 measured by the adjacent photodiodes 29 is set to be larger than 0.1 actually 0.6 as expressed by the following conditional expression:

$$F = \frac{f}{p} = \frac{p - C_u}{p \cdot C_u} \cdot C_l > 0.1$$

Therefore, even if the position shifts or deformations of the predetermined sections 37 measured by the individual photodiodes 29 occur according to the manufacturing and assembling errors of optical parts, the overlap of the adjacent predetermined sections 37 is ensured. No dead area is generated in the predetermined sections to be measured, and the extremely high sensitivity regions are not liable to be generated. The amount of incident light on the photodiodes 29 is increased.

The original film 21 is often warped due to the condition of development or the like, so that a film contact failure phenomenon occurs in which the original film 21 is partially apart from the film stand 22. However, the larger overlap of the adjacent predetermined sections 37 accomplishes the smaller measuring error due to the film contact failure phenomenon.

The apparatus is adapted to satisfy the following conditional expressions:

$$1.05 > J > 0.95$$

$$J = \frac{S \cdot p}{H \cdot C_u}$$

Therefore, the composition of the sensitivity in the overlapping part of the predetermined sections 37 measured by the adjacent photodiodes 29 is substantially equal to the sensitivity in the non-overlapping part. The comprehensive sensitivity 39 of the photodiodes 29 on the original film 21 is formed to be substantially horizontal except at both ends thereof.

The light which causes internal reflection in the light detecting unit 24, such as undesirable incident light 53 shown in FIG. 3, is blocked by the middle stopping plate 31 so as to be prevented from being incident on the photodiodes 29.

Hereinabove described is the operation where the photodiodes 29 are arranged one-dimensionally in the main scanning direction X to travel in the sub-scanning direction Y. A similar discussion can be applied to the operation where the photosensitive elements such as photodiodes are arranged two-dimensionally (in the X and Y directions). In the case where the photodiodes 29 are arranged one-dimensionally in the main scanning direction X to travel in the sub-scanning direction Y, the substitution of a reading distance for the distance p in the expressions (2) and (3) with respect to the sub-scanning direction Y can produce an effect similar to the operation in the two-dimensional arrangement of the photodiodes 29.

Figure 13:
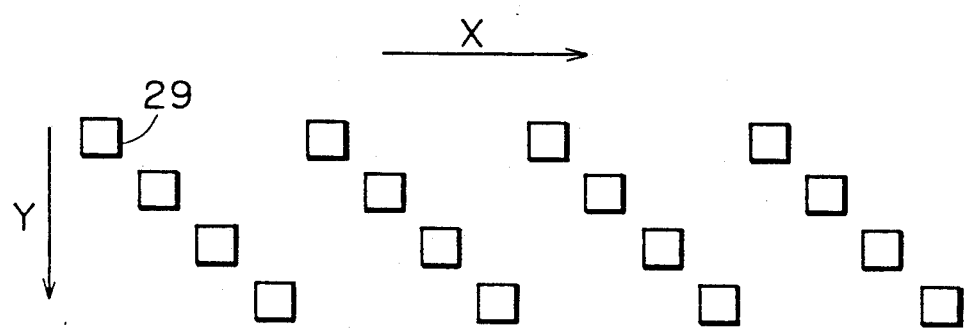
FIGS. 13 and 14 show examples of arrangements of photosensitive elements in the apparatus of the present invention, respectively.
Figure 14:
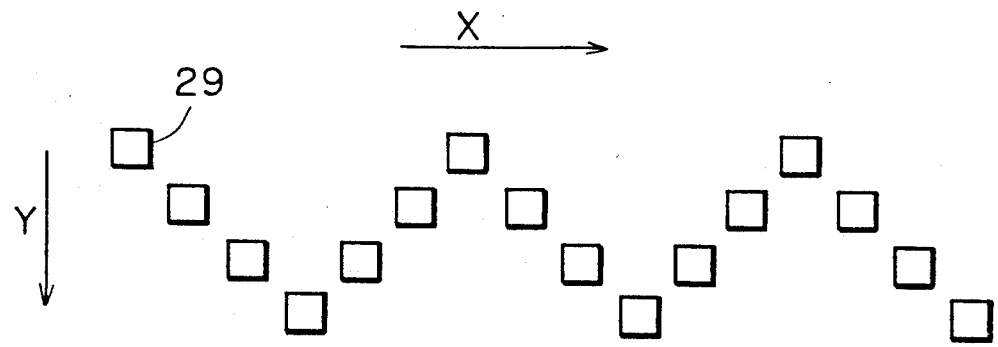
Figure 15:
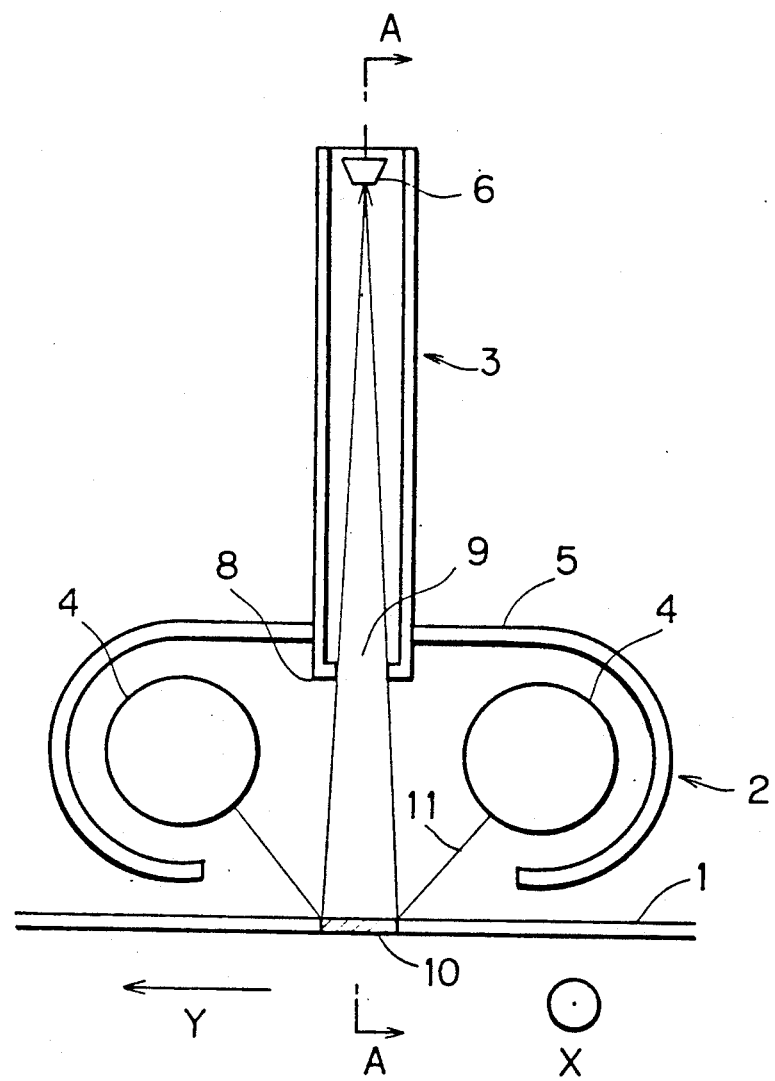
FIG. 15 is a cross-sectional view of a measuring head for a conventional apparatus taken along the plane perpendicular to a main scanning direction.
Figure 16:
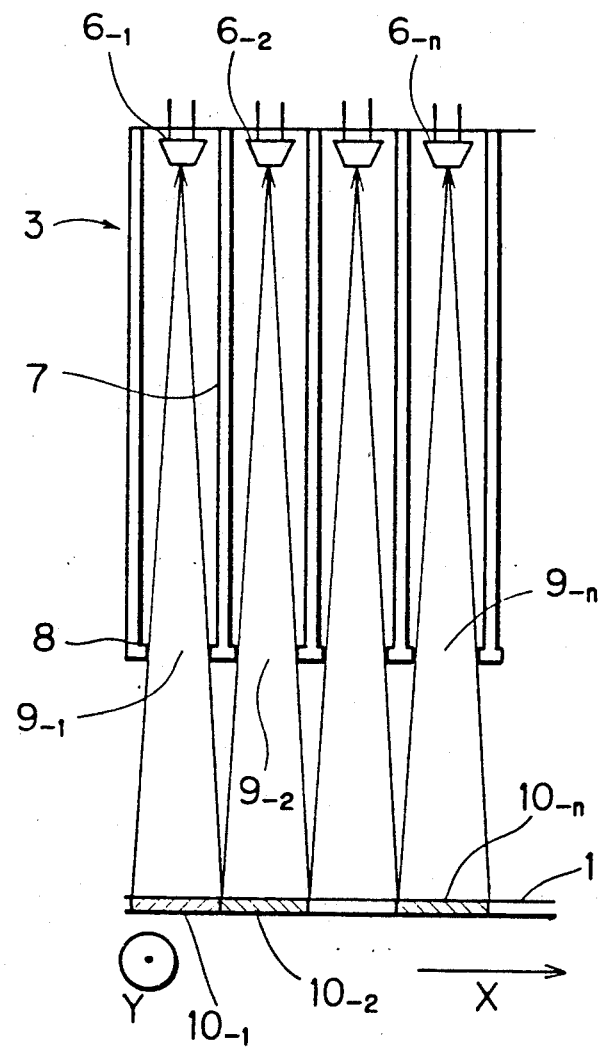
FIG. 16 is a cross-sectional view taken along the line A—A of FIG. 15.

In the preferred embodiment, the photodiodes 29 are arranged linearly in the main scanning direction X. The photodiodes 29 may be arranged in a zigzag as shown in FIGS. 13 and 14. Even if the width of an electric circuit group corresponding to a single measuring set in the main scanning direction X is relatively large compared with the distance p between the photodiodes 29, such a zigzag arrangement can produce an equivalent effect to the arrangement of the respective measuring sets in the main scanning direction X at a predetermined pitch smaller than the width of the electric circuit group. In this case, since the photodiodes 29 are arranged in a form relatively shifted in the sub-scanning direction Y, the read timing of the respective photodiodes 29 must be adjusted according to the shifts.

The influence of the overlapping factor F on the measuring error caused by the production of the manufacturing or assembling error of the parts is examined hereinafter. As the overlapping factor F is increased, the influence of the manufacturing or assembling error of the parts on the measuring error is increased in some cases and decreased in other cases.

Generally, when the overlapping factor F is large, the influence of the errors in the effective distances H and S shown in FIGS. 4 and 7 on the measuring error is small. In particular, the unevenness and warping of the image bearing member 21 and the fluctuation in height in the traveling of the measuring head 25 (in FIG. 1) result in the error in the effective distance H. The influence of the warping is large when the image bearing member 21 is an original film, and the influence of the unevenness is large when the image bearing member 21 is a printing plate. A large error in the effective distance H must be estimated, unless the flatness of the image bearing member 21 is ensured, for example, by sandwiching the image bearing member 21 between two flat plates. With printing plates, which are in common made of metal, it is difficult to obtain high flatness. The measuring error due to the error in the effective distance H accounts for a large proportion in the whole measuring errors.

The measuring error due to the error in the effective dimension $C_u$ of the apertures 33 of the stopping plate 30 is small when the overlapping factor F is large. The manufacture by means of a processing method with particularly high accuracy, such as laser cutting and etching, cannot be free from the manufacturing error of about several $\mu m$ to tens of $\mu m$. Even such a small error exerts not a little influence on the measuring error.

On the other hand, the measuring error due to the errors in the distance between the centers of the adjacent photosensitive elements 29 and in the distance between the centers of the adjacent apertures 33 of the stopping plate 30 is large when the overlapping factor F is large. If the stopping plate 30 is manufactured by such a processing method as laser cutting or etching, the error in the distance between the centers of the adjacent apertures 33, which is at most several $\mu m$, can be smaller than the error in the effective dimension $C_u$ of the apertures 33 generally by approximately one figure. The measuring error due to the error in the distance between the centers of the adjacent apertures 33 is accordingly small. The error in the distance between the centers of the adjacent photosensitive elements 29 can be restricted by the use of the second stopping plate 32, as described above.

Thus, when the overlapping factor F is large, the influence of the manufacturing or assembling error of the parts on the measuring error is large in some cases and small in other cases depending on the manufacturing or assembling method. It is not necessarily determinable that the measuring error is small when the overlapping factor F is large. For obtaining certain measuring accuracy or more, it is common to manufacture the stopping plates 30 and 32 by a method in which errors are small. On the other hand, it is difficult to restrain the unevenness of the printing plates. The error according to the fluctuation in height which accompanies the travel of the measuring head 25 is liable to be large, compared with the manufacturing error of the parts. Taking the above into account, it is considered that the measuring error is more often small when the overlapping factor F is large.

As the overlapping factor F is increased, the length $m_2$ of one side of the predetermined sections $37_{-1}$ to $37_{-3}$ measured by the respective photosensitive elements $29_{-1}$ to $29_{-3}$ is increased. The spatial resolution accordingly tends to deteriorate. Preferably the overlapping factor F does not exceed 1.

The functions of the obstructors 36 are examined hereinafter. The obstructors 36 are provided to prevent undesirable incident light coming from the apertures 33 and 34 corresponding to a predetermined photodiode 29 from being incident directly on the neighboring photodiode 29. The use of the obstructors 36 is particularly effective when a small number of middle stopping plates 31 are used and the effective dimensions $C_u$ and $C_l$ of the first and second stopping plates 30 and 32 are relatively large compared with the distance p between the photodiodes 29, as in the preferred embodiment. In other words, if the distance p is sufficiently (e.g., three times or more) larger than the effective dimensions $C_u$ and $C_l$ and a large number of (e.g., three or more) middle stopping plates 31 are provided at suitable positions, the undesirable incident light can be prevented from being incident directly on the photodiodes 29. In this case, the obstructors 36 are not necessarily required. As the effective dimensions $C_u$ and $C_l$ are decreased, in general, the influence of a manufacturing error in the effective dimensions $C_u$ and $C_l$ of the stopping plates 30 and 32 on the measuring error is increased, and the amount of incident light on the photodiodes 29 is decreased. It is hence preferable that the effective dimensions $C_u$ and $C_l$ are as large as possible. As for the obstructors 36, no particular accuracy is required for processing, and the restriction of thickness is lax. As for the middle stopping plates 31, on the other hand, considerably high processing accuracy of the apertures 35 (in particular, the distance between the apertures 35) is required. The thickness of the middle stopping plates 31 must be small so that the reflection at the internal walls of the apertures 35 is disregarded. The middle stopping plates 31 thereby tend to be considerably expensive. It is not necessarily expedient to indiscreetly employ a large number of middle stopping plates 31.

For this reason, the obstructors 36 are often provided between the photodiodes 29 in a manner shown in FIG. 3. The obstructors 36, however, reflect light unless a special coating or chemical treatment is provided on the surface thereof. This causes a measuring error in many cases. The influence of such undesirable incident light can be reduced by providing the middle stopping plate 31 having the apertures 35 the size of which is designed not to prevent the regular light passing through the corresponding apertures 33 and 34 of the first and second stopping plates 30 and 32 in the manner shown in FIG. 3.

Higher effect can be given if the number of middle stopping plates 31 is increased within the range in which the reflection at the internal walls of the apertures 35 can be disregarded. Since the problem of costs occurs as mentioned above, the number of middle stopping plates 31 is preferably adapted so that the influence of the undesirable incident light on the measuring error is ignorable (e.g., 0.1% or less). In the preferred embodiment, a single middle stopping plate 31 is employed. For increasing the dimensions of the apertures 33 to 35 of the respective stopping plates 30 to 32, it is desirable to equalize the distances between the first stopping plate 30 and the middle stopping plate 31, between the second stopping plate 32 and the middle stopping plate 31 and between the respective middle stopping plates 31.

In the above-mentioned preferred embodiment, a system of measuring the light transparency of the image bearing member 21 is discussed. However, a system of measuring light reflectivity is applicable. In this system, the light source 26 is disposed on the same side as the first stopping plate 31, the photodiodes 29 and others relative to the image bearing member 21. The light source 26 is positioned such that it does not prevent the light reflected from the image bearing member 21 and incident on the photodiodes 29. When the image bearing member 21 is transparent, a reflecting sheet for scattering light must be provided on the opposite side of the light source 26, the photodiodes 29 and others.

Although the present invention has been described and illustrated in detail, it is clearly understood that the same is by way of illustration and example only and is not to be taken by way of limitation. The spirit and scope of the present invention should be limited only by the terms of the appended claims.

What is claimed is:

1. An image reader for measuring light reflectivity or transparency of a predetermined section in an image bearing member, comprising:

a supporting means for supporting said image bearing member;

a light source for illuminating the predetermined section to be measured in said image bearing member;

a plurality of photosensitive elements one- or two-dimensionally arranged substantially in parallel with said image bearing member;

a first stopping plate disposed between said photosensitive elements and said image bearing member and provided with apertures at positions corresponding to said photosensitive elements;

a second stopping plate disposed between said photosensitive elements and said first stopping plate and provided with apertures which are smaller in size than photosensitive surfaces of said photosensitive elements, and which are at positions corresponding to said photosensitive elements; and a computation means for finding the average light reflectivity or transparency of the predetermined section based on the output signal of the corresponding photosensitive elements, said image reader satisfying the following expression:

$$S' < \frac{C_p - C_l}{C_u - C_l} S$$

where $S'$: an effective distance between the photosensitive surfaces of said photosensitive elements and the apertures of said second stopping plate $S$: an effective distance between the apertures of said second stopping plate and the apertures of said first stopping plate $C_u$: an effective dimension of the apertures of said first stopping plate $C_l$: an effective dimension of the apertures of said second stopping plate $C_p$: an effective dimension of the photosensitive surfaces of said photosensitive elements.

2. An image reader as set forth in claim 1, wherein an overlapping factor F of the predetermined sections which are measured by adjacent photosensitive elements exceeds 0.1, the overlapping factor F being determined by the following expression, and a flat factor J of sensitivity of the predetermined section to be measured is more than 0.95 and less than 1.05, the flat factor J being determined by the following expression:

$$F = \frac{(p - C_u) \cdot C_l}{p \cdot C_u}$$

$$J = \frac{S \cdot p}{H \cdot C_u}$$

where p: a distance between centers of adjacent apertures of said second stopping plate $C_u$: an effective dimension of the apertures of said first stopping plate $C_l$: an effective dimension of the apertures of said second stopping plate H: an effective distance between the apertures of said second stopping plate and said image bearing member S: an effective distance between the apertures of said second stopping plate and the apertures of said first stopping plate.

3. An image reader as set forth in claim 2, wherein said light source, said first stopping plate, said second stopping plate and said photosensitive elements are integrated to form a measuring head.

4. An image reader as set forth in claim 3, further comprising a moving means for moving one of said image bearing member and said measuring head relative to the other.

5. An image reader as set forth in one of claims 1, 2 or 4, further comprising a shading correction means for correcting substantially the sensitivities of at least two or more measuring sets to be the same value, the measuring sets being formed with components ranging from the corresponding parts of said light source to the corresponding parts of said computation means.

6. An image reader as set forth in claim 5, wherein said shading correction means further includes at least one or more calibration strips having known reflectivity or transparency, each of said calibration strips having an area equal to or larger than said predetermined sections which are measured by said at least two or more photosensitive elements.

7. An image reader as set forth in claim 5, further comprising one or more middle stopping plates disposed between said first stopping plate and said second stopping plate and provided with apertures at positions corresponding to said photosensitive elements, the apertures of said one or more middle stopping plates having a configuration which does not interrupt light incidence from the apertures of said first stopping plate through the apertures of said second stopping plate onto said photosensitive elements.

8. An image reader as set forth in claim 7, further comprising an obstructor disposed between said photosensitive elements adjacent to each other at least in one spacing between two adjacent stopping plates selected from the group consisting of said first stopping plate, said one or more middle stopping plates and said second stopping plate.

9. An image reader as set forth in one of claims 1, 2, 3 or 4, wherein said photosensitive elements are arranged in a matrix.

10. An image reader as set forth in one of claims 1, 2, 3 or 4, wherein said photosensitive elements are arranged in a zigzag.

11. An image reader as set forth in claim 5, wherein said photosensitive elements are arranged in a matrix.

12. An image reader as set forth in claim 6, wherein said photosensitive elements are arranged in a matrix.

13. An image reader as set forth in claim 7, wherein said photosensitive elements are arranged in a matrix.

14. An image reader as set forth in claim 8, wherein said photosensitive elements are arranged in a matrix.

15. An image reader as set forth in claim 5, wherein said photosensitive elements are arranged in a zigzag.

16. An image reader as set forth in claim 6, wherein said photosensitive elements are arranged in a zigzag.

17. An image reader as set forth in claim 7, wherein said photosensitive elements are arranged in a zigzag.

18. An image reader as set forth in claim 8, wherein said photosensitive elements are arranged in a zigzag.

* * * * *